US010500060B2

(12) United States Patent
Bernhardt, Jr. et al.

(10) Patent No.: US 10,500,060 B2
(45) Date of Patent: *Dec. 10, 2019

(54) DISC PREPARATION INSTRUMENT FOR USE IN SPINAL FUSION

(71) Applicant: SPINE WAVE, INC., Shelton, CT (US)

(72) Inventors: Andrew Bernhardt, Jr., Florence, SC (US); David Considine, Stratford, CT (US); David Boisvert, Southington, CT (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/946,910

(22) Filed: Apr. 6, 2018

(65) Prior Publication Data

US 2018/0221169 A1    Aug. 9, 2018

Related U.S. Application Data

(62) Division of application No. 15/454,287, filed on Mar. 9, 2017, now Pat. No. 9,937,055.

(Continued)

(51) Int. Cl.
*A61F 2/44* (2006.01)
*A61F 2/46* (2006.01)
*A61F 2/30* (2006.01)

(52) U.S. Cl.
CPC .......... *A61F 2/4455* (2013.01); *A61F 2/447* (2013.01); *A61F 2/4611* (2013.01);

(Continued)

(58) Field of Classification Search
CPC ...... A61F 2/4455; A61F 2/447; A61F 2/4611; A61F 2/4684; A61F 2/30744;

(Continued)

(56) References Cited

U.S. PATENT DOCUMENTS 2,998,007 A    8/1961    Herzog
3,574,381 A    4/1971    Ocheltree et al.
(Continued)

FOREIGN PATENT DOCUMENTS

EP    0 064 724 A2    11/1982
FR    2827156 A1    1/2003

OTHER PUBLICATIONS

International Search Report for PCT/US2018/054092, dated Dec. 31, 2018.
Written Opinion for PCT/US2018/054092, dated Dec. 31, 2018.

*Primary Examiner* — Pedro Philogene
(74) *Attorney, Agent, or Firm* — Hoffmann & Baron, LLP

(57) ABSTRACT

A system for fusing together opposing vertebra of a spine that defines a disc space therebetween. The system comprises a disc preparation instrument and an inserter assembly for use in the interbody fusion procedure. Disc preparation instrument comprises an elongate handle supporting a trial device at one end thereof. Inserter assembly comprises an elongate inserter supporting at one end thereof an interbody cage implant for insertion into the disc space. Disc preparation instrument provides a scoring element that scribes vertebral endplates at an appropriate scored location for anchor blades on the cage implant to engage the vertebral bodies. Inserter is used to introduce cage implant with anchor blades into the disc space to an appropriate depth so that the blades will be precisely positioned at the scored location created by the scoring element for penetration into the vertebral endplates.

17 Claims, 15 Drawing Sheets

Related U.S. Application Data

(60) Provisional application No. 62/426,899, filed on Nov. 28, 2016.

(52) U.S. Cl.
CPC ........ *A61F 2/4684* (2013.01); *A61F 2/30744* (2013.01); *A61F 2002/30131* (2013.01); *A61F 2002/30579* (2013.01); *A61F 2002/30841* (2013.01); *A61F 2002/4627* (2013.01); *A61F 2002/4629* (2013.01)

(58) Field of Classification Search
CPC .. A61F 2/30749; A61F 2/4657; A61F 2/4425; A61F 2002/30131; A61F 2002/30579; A61F 2002/30841; A61F 2002/4627; A61F 2002/4629; A61F 2002/30507; A61F 2002/4623; A61F 2002/30578; A61B 17/86
USPC ........... 623/17.11–17.16; 606/246–279, 102, 606/104, 105, 100, 99, 96, 86 A, 86 B, 606/86 R See application file for complete search history.

(56) References Cited

U.S. PATENT DOCUMENTS

| | | |
|---|---|---|
| 3,814,089 A | 6/1974 | Deyerle |
| 4,275,717 A | 6/1981 | Bolesky |
| 4,519,100 A | 5/1985 | Wills et al. |
| 4,667,664 A | 5/1987 | Taylor et al. |
| 4,848,327 A | 7/1989 | Perdue |
| 4,892,545 A | 1/1990 | Day et al. |
| 5,057,103 A | 10/1991 | Davis |
| 5,397,364 A | 3/1995 | Kozak et al. |
| 5,522,899 A | 6/1996 | Michelson |
| 5,534,004 A | 7/1996 | Santangelo |
| 5,601,550 A | 2/1997 | Esser |
| 5,782,830 A | 7/1998 | Farris |
| 5,800,550 A | 9/1998 | Sertich |
| 5,810,820 A | 9/1998 | Santori et al. |
| 5,971,986 A | 10/1999 | Santori et al. |
| 5,976,139 A | 11/1999 | Bramlet |
| 6,030,401 A | 2/2000 | Marino |
| 6,077,264 A | 6/2000 | Chemello |
| 6,099,531 A | 8/2000 | Bonutti |
| 6,120,503 A | 9/2000 | Michelson |
| 6,174,311 B1 | 1/2001 | Branch et al. |
| 6,179,873 B1 | 1/2001 | Zientek |
| 6,183,474 B1 | 2/2001 | Bramlet et al. |
| 6,235,059 B1 | 5/2001 | Benezech et al. |
| 6,342,057 B1 | 1/2002 | Brace et al. |
| 6,342,074 B1 | 1/2002 | Simpson |
| 6,379,364 B1 | 4/2002 | Brace et al. |
| 6,409,768 B1 | 6/2002 | Tepic et al. |
| 6,443,954 B1 | 9/2002 | Bramlet et al. |
| 6,447,546 B1 | 9/2002 | Bramlet et al. |
| 6,468,311 B2 | 10/2002 | Boyd et al. |
| 6,527,803 B1 | 3/2003 | Crozet et al. |
| 6,558,388 B1 | 5/2003 | Bartsch et al. |
| 6,558,423 B1 | 5/2003 | Michelson |
| 6,648,889 B2 | 11/2003 | Bramlet et al. |
| 6,770,096 B2 | 8/2004 | Bolger et al. |
| 7,056,344 B2 | 6/2006 | Huppert et al. |
| 7,223,289 B2 | 5/2007 | Trieu et al. |
| 7,232,464 B2 | 6/2007 | Mathieu et al. |
| 7,235,082 B2 | 6/2007 | Bartish et al. |
| 7,416,553 B2 | 8/2008 | Patel et al. |
| 7,594,931 B2 | 9/2009 | Louis et al. |
| 7,674,287 B2 | 3/2010 | Alferness et al. |
| 7,695,516 B2 | 4/2010 | Zeegers |
| 7,776,047 B2 | 8/2010 | Fanger et al. |
| 7,842,088 B2 | 11/2010 | Rashbaum et al. |
| 7,846,207 B2 | 12/2010 | Lechmann et al. |
| 7,909,829 B2 | 3/2011 | Patel et al. |
| 7,909,848 B2 | 3/2011 | Patel et al. |
| 7,935,123 B2 | 5/2011 | Fanger et al. |
| 7,988,693 B2 | 8/2011 | Martz et al. |
| 8,002,776 B2 | 8/2011 | Liu et al. |
| 8,062,303 B2 | 11/2011 | Berry et al. |
| 8,080,062 B2 | 12/2011 | Armstrong et al. |
| 8,147,556 B2 | 4/2012 | Louis et al. |
| 8,216,313 B2 | 7/2012 | Moore |
| 8,257,439 B2 | 9/2012 | Zeegers |
| 8,267,997 B2 | 9/2012 | Colleran |
| 8,268,000 B2 | 9/2012 | Waugh et al. |
| 8,273,127 B2 | 9/2012 | Jones et al. |
| 8,282,682 B2 | 10/2012 | Kirschman |
| 8,292,958 B1 | 10/2012 | Bruffey et al. |
| 8,313,528 B1 | 11/2012 | Wensel |
| 8,328,870 B2 | 12/2012 | Patel et al. |
| 8,328,872 B2 | 12/2012 | Duffield et al. |
| 8,343,219 B2 | 1/2013 | Allain et al. |
| 8,377,133 B2 | 2/2013 | Yuan et al. |
| 8,394,107 B2 | 3/2013 | Fanger et al. |
| 8,409,285 B2 | 4/2013 | Keller |
| 8,454,700 B2 | 6/2013 | Lemoine et al. |
| 8,460,388 B2 | 6/2013 | Kirwan et al. |
| 8,523,946 B1 | 9/2013 | Swann |
| 8,617,245 B2 | 12/2013 | Brett |
| 8,641,766 B2 | 2/2014 | Donner et al. |
| 8,685,104 B2 | 4/2014 | Lee et al. |
| 8,709,083 B2 | 4/2014 | Duffield et al. |
| 8,728,165 B2 | 5/2014 | Parry et al. |
| 8,840,651 B2 | 9/2014 | Reiley |
| 8,864,830 B2 | 10/2014 | Malandain |
| 8,906,101 B2 | 12/2014 | Lee et al. |
| 8,932,359 B2 | 1/2015 | Brett |
| 8,968,405 B2 | 3/2015 | Kirwan et al. |
| 9,033,993 B2 | 5/2015 | Bae et al. |
| 9,039,774 B2 | 5/2015 | Chataigner et al. |
| 9,044,337 B2 | 6/2015 | Dinville et al. |
| 9,078,765 B2 | 7/2015 | Louis et al. |
| 9,101,489 B2 | 8/2015 | Protopsaltis et al. |
| 9,155,631 B2 | 10/2015 | Seifert et al. |
| 9,161,841 B2 | 10/2015 | Kana et al. |
| 9,216,024 B2 | 12/2015 | Geisert et al. |
| 9,241,809 B2 | 1/2016 | McDonough et al. |
| 9,358,134 B2 | 6/2016 | Malandain |
| 9,402,740 B1 | 8/2016 | Donaldson |
| 9,402,741 B1 | 8/2016 | Donaldson |
| 9,572,685 B2 | 2/2017 | Perry |
| 9,937,055 B1* | 4/2018 | Bernhardt, Jr. ....... A61F 2/4455 |
| 2001/0011191 A1 | 8/2001 | Kohrs |
| 2004/0082955 A1 | 4/2004 | Zirkle, Jr. |
| 2007/0239168 A1 | 10/2007 | Kuenzi et al. |
| 2007/0250167 A1 | 10/2007 | Bray et al. |
| 2008/0243131 A1* | 10/2008 | Sorrenti ............... A61F 2/4611 606/99 |
| 2008/0249569 A1 | 10/2008 | Waugh et al. |
| 2008/0281425 A1 | 11/2008 | Thalgott et al. |
| 2009/0099601 A1 | 4/2009 | Aferzon et al. |
| 2009/0164020 A1 | 6/2009 | Janowski et al. |
| 2010/0016968 A1 | 1/2010 | Moore |
| 2010/0145459 A1 | 6/2010 | McDonough et al. |
| 2010/0185289 A1 | 7/2010 | Kirwan et al. |
| 2011/0098747 A1 | 4/2011 | Donner et al. |
| 2011/0208311 A1* | 8/2011 | Janowski .............. A61F 2/4465 623/17.16 |
| 2012/0078373 A1 | 3/2012 | Gamache et al. |
| 2012/0116466 A1 | 5/2012 | Dinville et al. |
| 2012/0191166 A1 | 7/2012 | Louis et al. |
| 2012/0197401 A1 | 8/2012 | Duncan et al. |
| 2012/0253406 A1 | 10/2012 | Bae et al. |
| 2012/0277872 A1 | 11/2012 | Kana et al. |
| 2012/0277873 A1 | 11/2012 | Kana et al. |
| 2013/0110242 A1 | 5/2013 | Kirwan et al. |
| 2013/0150968 A1 | 6/2013 | Dinville et al. |
| 2013/0226300 A1 | 8/2013 | Chataigner et al. |
| 2013/0245767 A1 | 9/2013 | Lee et al. |
| 2014/0088711 A1 | 3/2014 | Chin et al. |
| 2014/0114413 A1 | 4/2014 | Allain et al. |
| 2014/0142619 A1 | 5/2014 | Serina et al. |

(56) References Cited

U.S. PATENT DOCUMENTS

| | | |
|---|---|---|
| 2014/0156010 A1 | 6/2014 | Lee et al. |
| 2014/0163684 A1 | 6/2014 | Donner et al. |
| 2014/0277456 A1 | 9/2014 | Kirschman |
| 2014/0277477 A1 | 9/2014 | Malandain |
| 2015/0051702 A1 | 2/2015 | Chataigner et al. |
| 2015/0051704 A1 | 2/2015 | Duffield et al. |
| 2015/0057754 A1 | 2/2015 | Reed et al. |
| 2015/0127107 A1 | 5/2015 | Kim et al. |
| 2015/0127109 A1 | 5/2015 | Brett |
| 2015/0202051 A1* | 7/2015 | Tanaka .................. A61F 2/447 623/17.16 |
| 2015/0209089 A1 | 7/2015 | Chataigner et al. |
| 2015/0305883 A1 | 10/2015 | Garber et al. |
| 2015/0305887 A1 | 10/2015 | McAtamney et al. |
| 2016/0015523 A1 | 1/2016 | Lewis et al. |
| 2016/0051372 A1* | 2/2016 | Pimenta ............... A61F 2/4455 623/17.16 |
| 2016/0151166 A1 | 6/2016 | Morris et al. |
| 2017/0112631 A1* | 4/2017 | Kuyler ................. A61F 2/4455 |

\* cited by examiner

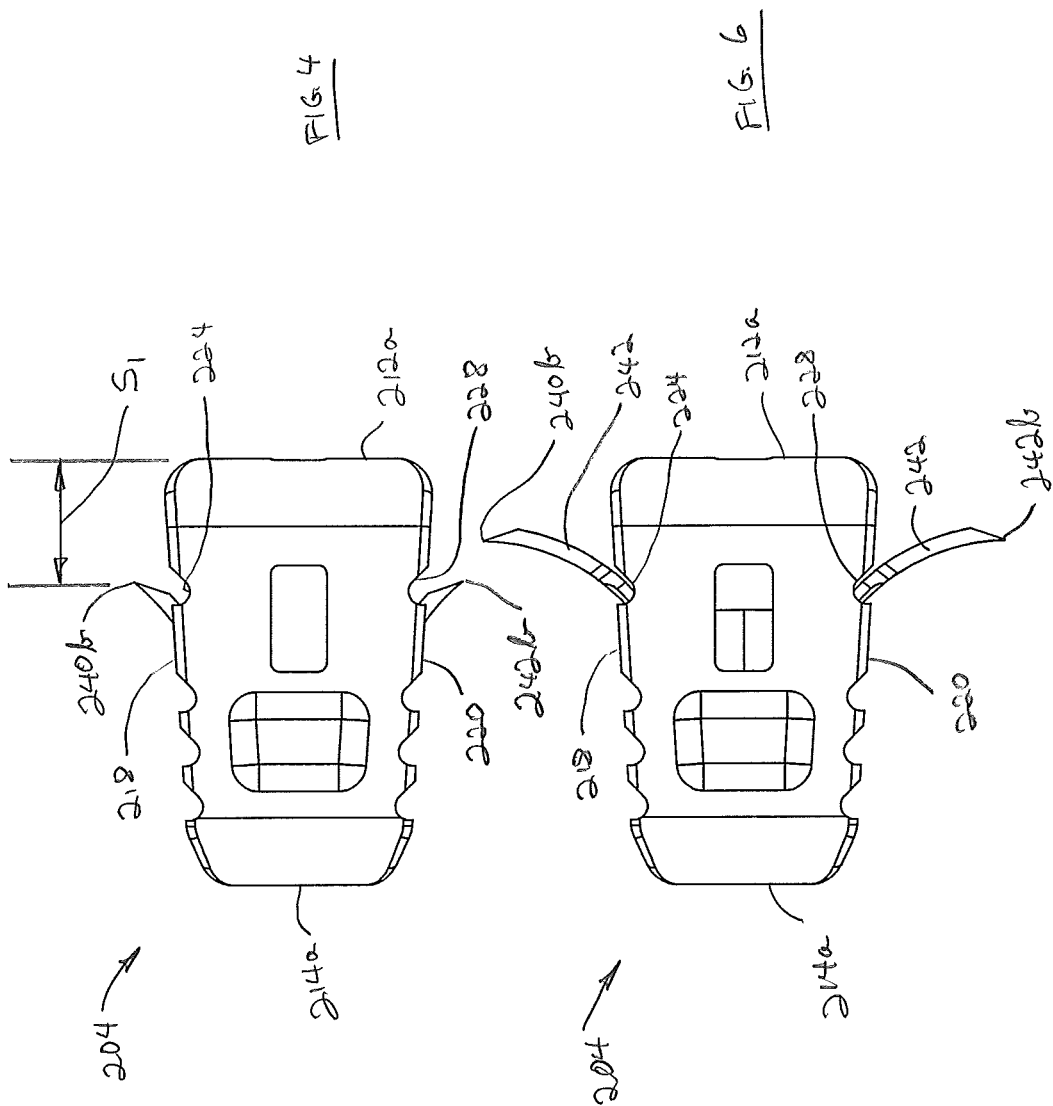

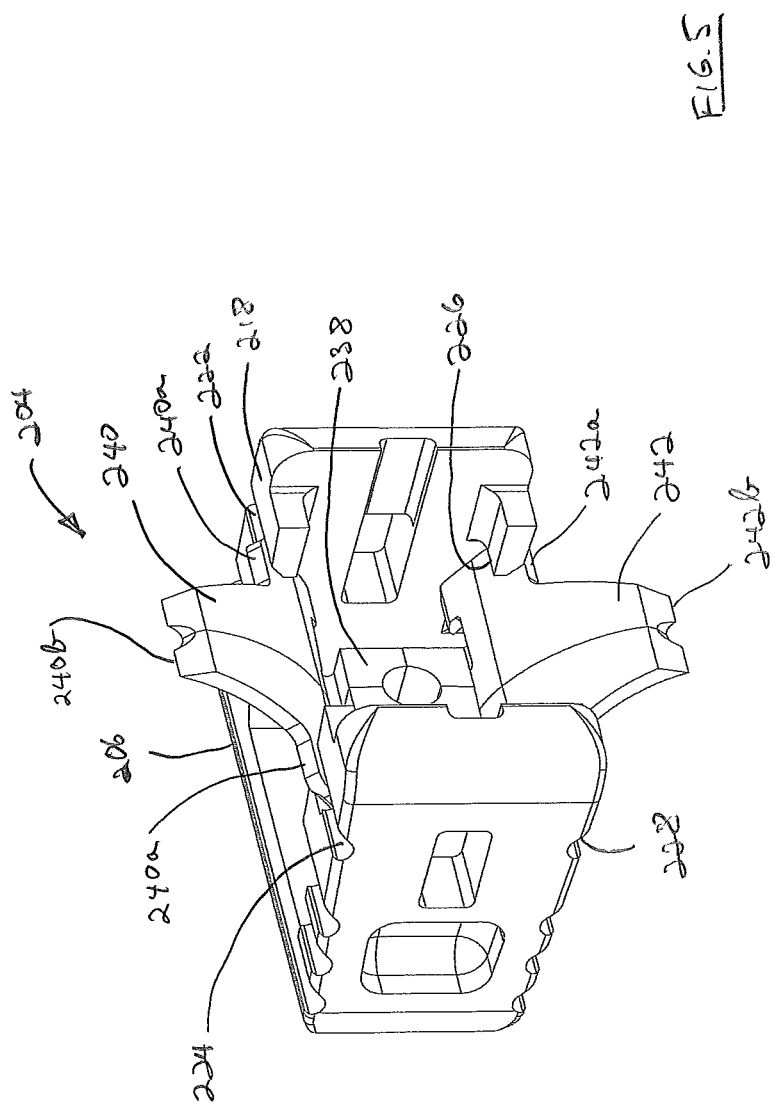

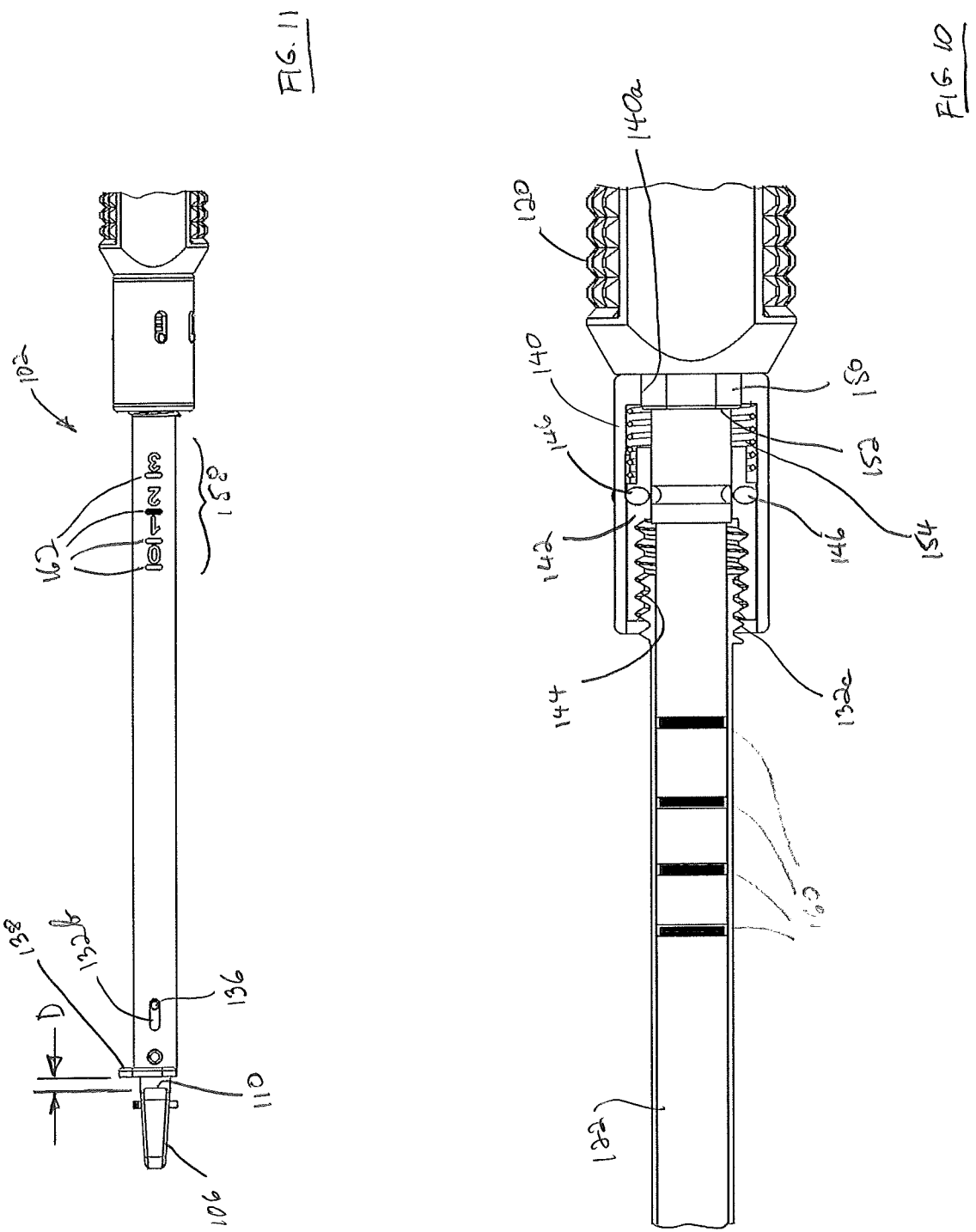

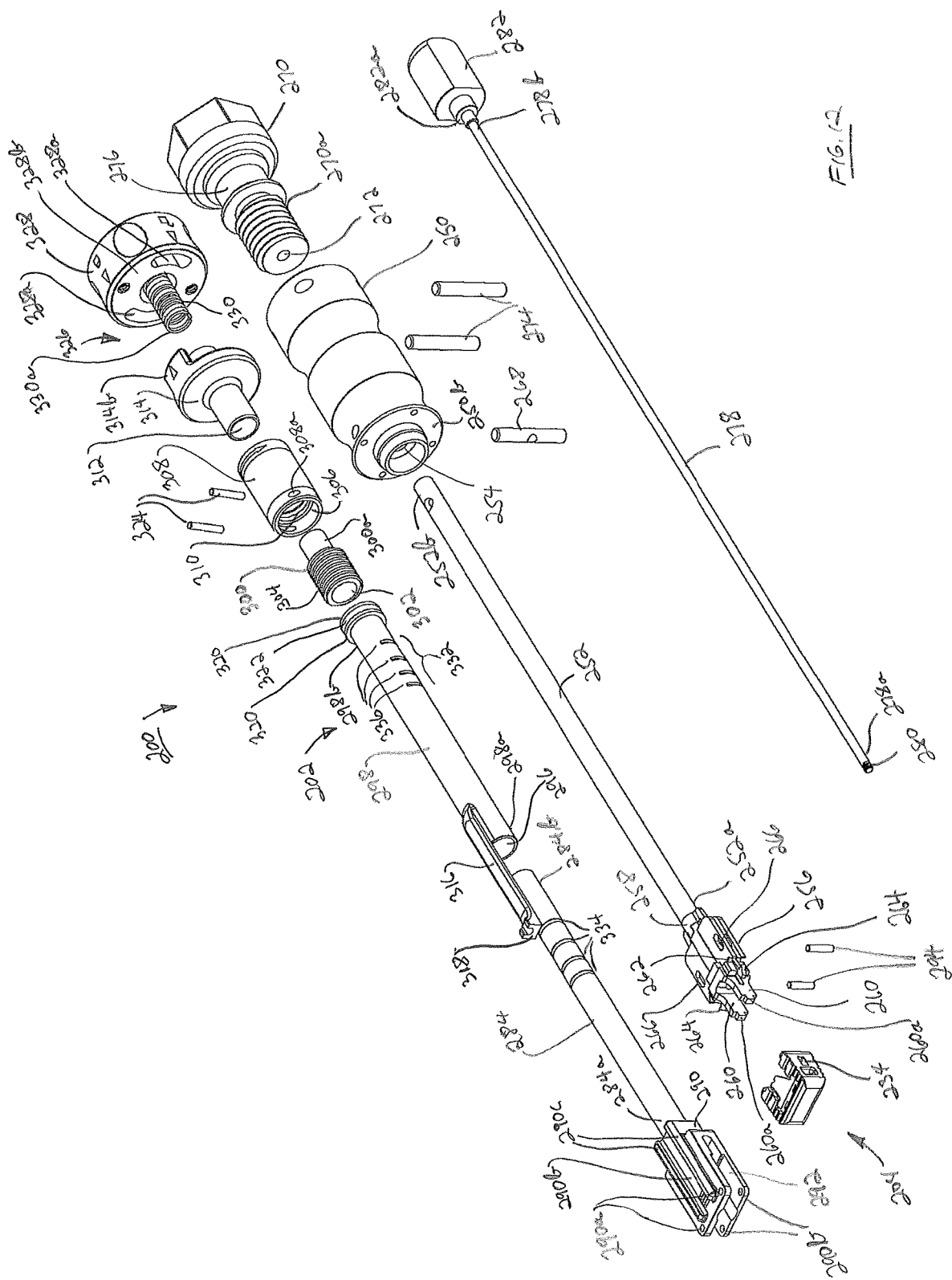

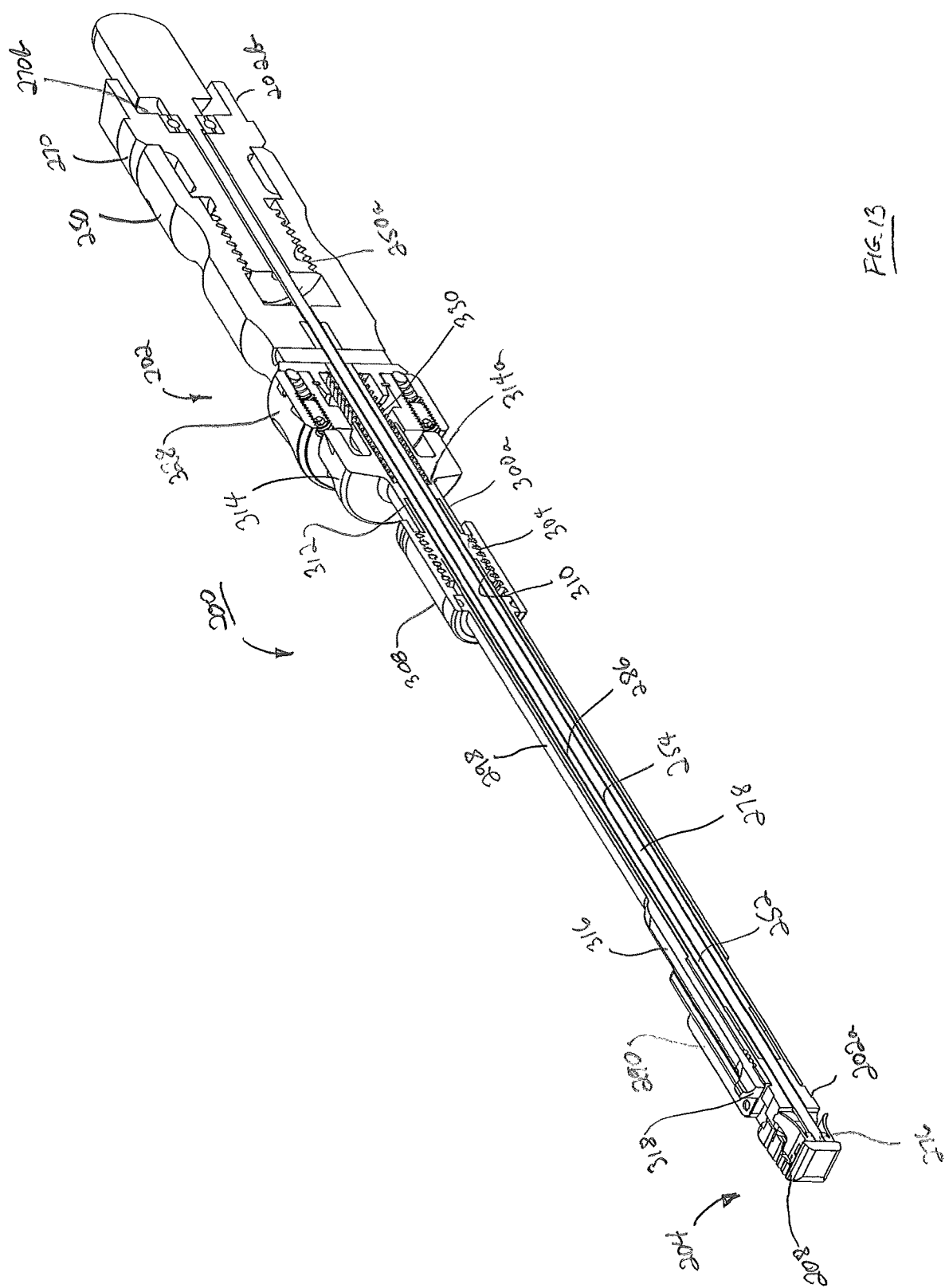

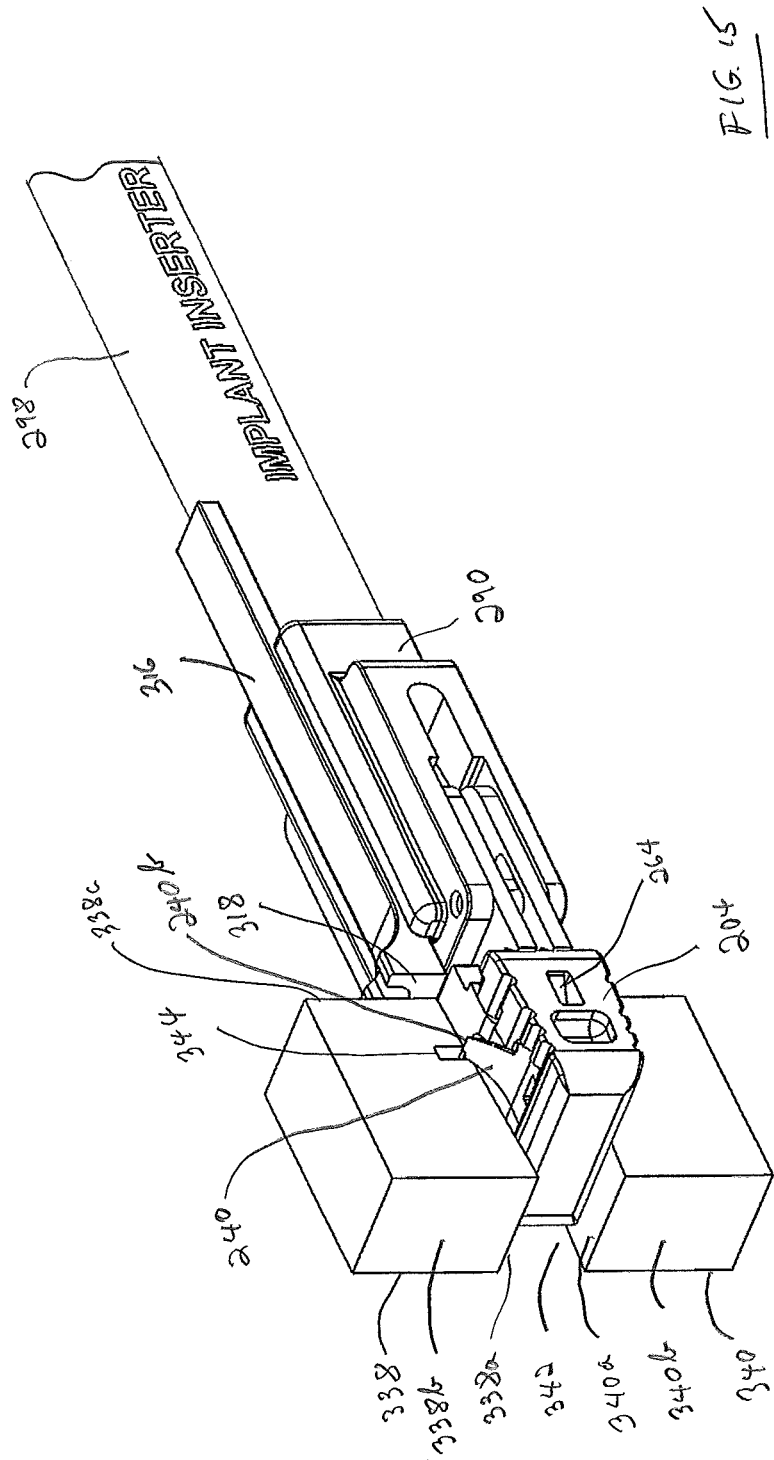

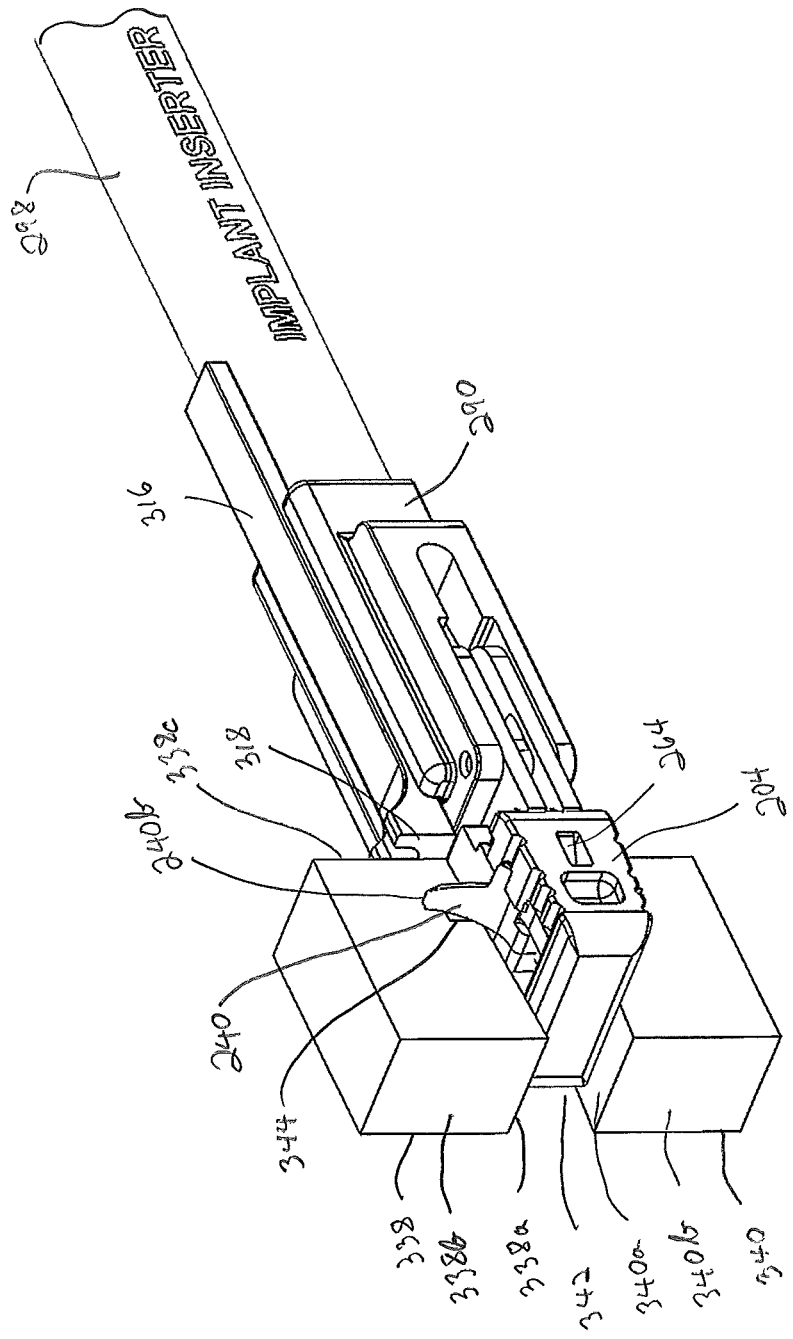

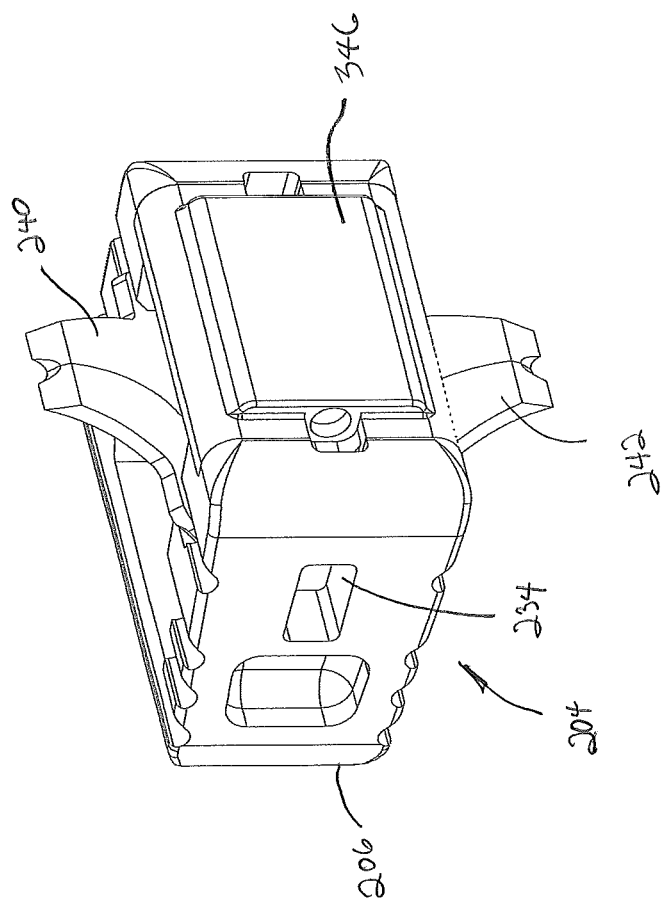

DISC PREPARATION INSTRUMENT FOR USE IN SPINAL FUSION

CROSS-REFERENCE TO RELATED APPLICATION

This is a divisional application of U.S. application Ser. No. 15/454,287, filed Mar. 9, 2017, now U.S. Pat. No. 9,937,055, which claims the benefit of U.S. Provisional Patent Application No. 62/426,899, filed Nov. 28, 2016, the entire contents of which are incorporated by reference herein.

FIELD OF THE INVENTION

The subject invention relates to the field of spinal fusion, and more particularly, to delivery systems for, and methods of, delivering and implanting spinal implants in a spinal column in the treatment of a spinal condition, including spinal fusion.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent the device in order to promote fusion between two adjacent vertebrae.

One embodiment of a spinal fusion device is described in U.S. Patent Publication No. 2015/0202051, entitled "Spinal Fusion System", filed on Jan. 16, 2015 by Shigeru Tanaka et al. (the '051 Application) and assigned to the same assignee as the subject application. The spinal fusion system described in the '051 Application includes an interbody fusion cage, a fixation plate, and an implanter. The fixation plate is receivable in an open volume of the interbody fusion cage and includes a superior blade and an inferior blade. The fixation plate is displaceable between a non-deployed state and a deployed state, wherein, when the fixation plate is received in the open volume and the fixation plate is in the non-deployed state, the superior and inferior blades extend generally parallel to each other. When the fixation plate is in the deployed state, the superior and inferior blades extend oppositely from each other into the endplates of opposing vertebral bodies. In a particular arrangement, the system may further include a trial/sizer tool including a set of trial/sizer instruments. Such instruments may incorporate a pre-scoring blade to break the vertebral endplate prior to insertion of the spinal implant into the disc space and deployment of the blades into the endplates. Thus, a trial device may serve two purposes, namely to test a size for a potential interbody fusion cage implant and to prepare one or more vertebral endplate surfaces for receiving the implant. The entire contents of the '051 Application are incorporated herein by reference.

While a trial device with a pre-scoring blade is beneficial, a system having the capability of precisely correlating the entry location of an anchor blade into the vertebral endplate of one or more vertebral bodies with the pre-scored location of such endplates is desirable.

SUMMARY OF THE INVENTION

It is an object of the invention to provide an improved system for fusing together a superior vertebra and an inferior vertebra. The system includes a disc preparation instrument that provides both a trialing function to aid in selection of an appropriate size implant for the intended spinal disc space and an endplate scoring function that scribes the vertebral endplates at an appropriate anterior-posterior position for the anchor plates of the spinal implant to engage the vertebral bodies. The instrument in one arrangement includes a trial device on one end that approximates the size and shape of the cage implant, a depth stop element to limit over-insertion into the disc space, and a rotating rasp element to slot the surfaces of the vertebral endplates on the superior and inferior faces at a controlled distance from the depth stop. The relative distance between the proximal face of the implant trial and the depth stop is adjustable in order to countersink the implant trial to a preferred depth with readable values (0, 1, 2, etc.). The scoring element is positioned within the implant trial at a location suitable for creating slots in the vertebral endplates that correspond to entry locations for blades on an anchor plate to penetrate the vertebral endplates. The scoring element is actuated rotationally about the long axis of the instrument by a turning a handle at the opposite end of the device in an oscillating fashion.

An implant inserter is used to introduce the interbody fusion cage implant with an anchor plate into the disc space to an appropriate depth so that blades on the anchor plate will be deployed into the slots created by the scoring element of the implant trial. The adjustable depth stop also includes readable values (0, 1, 2, etc.) that correspond to the depth settings on the implant trial. Intended use requires that the depth setting on the inserter matches the depth setting on the implant trial in order to position the implant at the appropriate depth. With a pull rod, the implant inserter also provides a mechanism to deploy the anchor plate.

DESCRIPTION OF THE FIGURES

FIG. 4 is a side elevational view of the cage implant of FIG. 3 with the anchor plate being in the first non-deployed position.

FIG. 5 is a top perspective view of the assembled cage implant of FIG. 2 with the anchor plate being disposed in a second deployed position.

FIG. 6 is a side elevational view of the cage implant of FIG. 5 with the anchor plate being in the second deployed position.

FIG. 10 is an enlarged partial view of the sectional view of the disc preparation instrument of FIG. 8 illustrating details of a depth indicator device.

FIG. 11 is a partial side elevational view of the distal end disc preparation instrument showing an example of a reading on the depth indicator device of FIG. 10 as it relates to the spacing between the proximal surface on the trial device and adjustable depth stop of the disc preparation instrument.

FIG. 12 is a top perspective exploded view of the inserter assembly of the system shown in FIG. 1.

FIG. 13 is a perspective longitudinally sectioned view of the inserter assembly of FIG. 12.

FIG. 15 is a perspective view showing the partially sectioned vertebral bodies of FIG. 14 and the distal end of the inserter assembly with the cage implant positioned in the intradiscal space and the penetration tips of the anchor plate being in a first non-deployed position in alignment with the scored location formed in the vertebral endplates.

FIG. 16 is a perspective view showing the partially sectioned vertebral bodies of FIG. 14 and the distal end of the inserter assembly with the cage implant positioned in the intradiscal space and the penetration tips of the anchor plate being in a second deployed position penetrating the vertebral bodies through the scored location formed in the vertebral endplates.

FIG. 17 is a top perspective view of the cage implant of FIG. 5 with the anchor plate in a second deployed position and including a cap thereon for bone graft retention.

DESCRIPTION OF THE EMBODIMENTS

Figure 1:
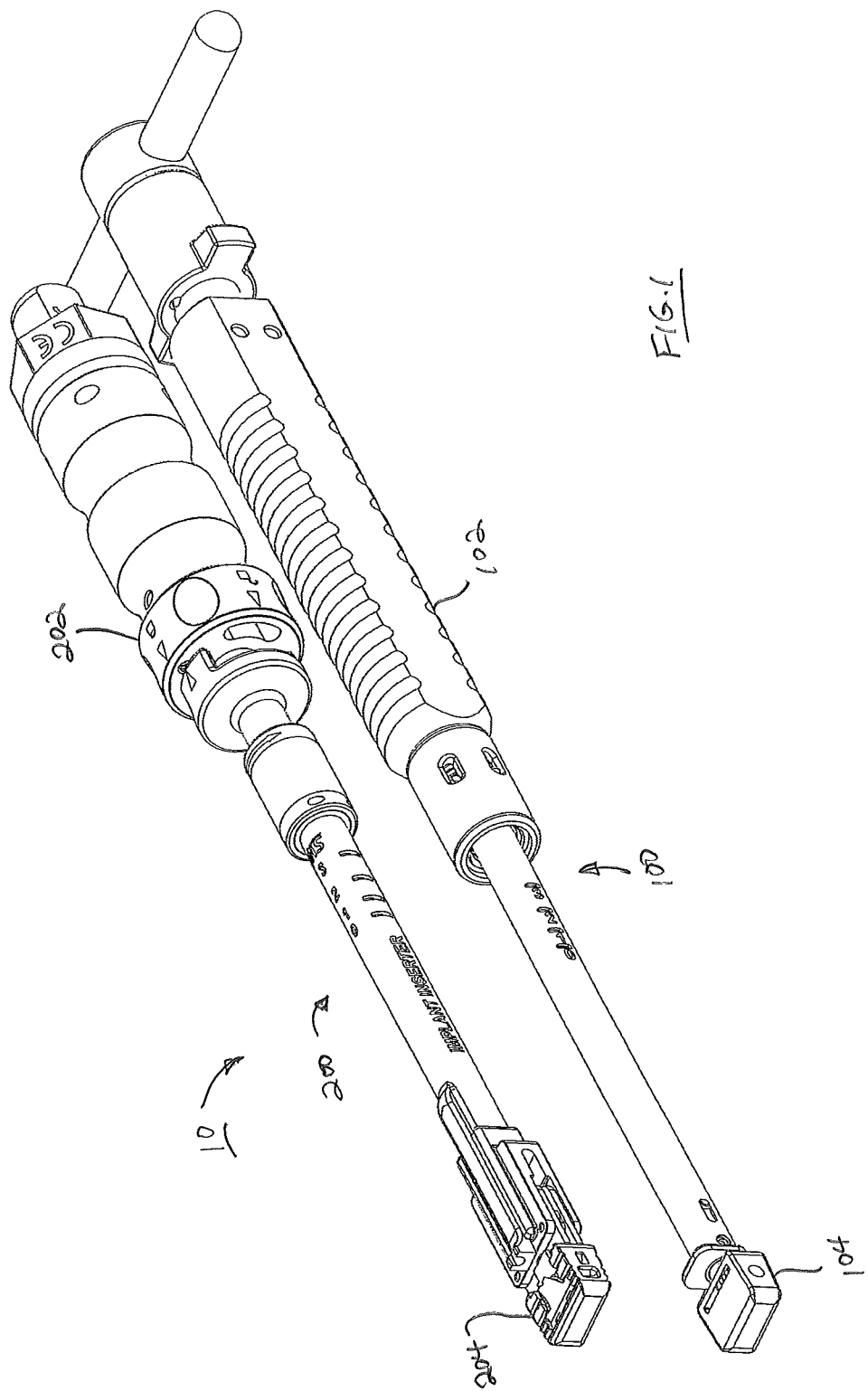
FIG. 1 is a top perspective view of a system, in accordance with one embodiment of the present invention, comprising a disc preparation instrument and an inserter assembly for fusing together opposing vertebra of a spine.

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring now to FIG. 1, a system 10 is shown for fusing together opposing vertebra of a spine that defines a disc space therebetween. System 10 comprises a disc preparation instrument 100 and an inserter assembly 200 for use in the interbody fusion procedure. Disc preparation instrument 100 comprises an elongate handle 102 supporting a trial device 104 at one end thereof. Inserter assembly 200 comprises an elongate inserter 202 supporting at one end thereof an interbody cage implant 204 for insertion into the disc space. Disc preparation instrument 100 provides a scoring element that scribes vertebral endplates at an appropriate anterior-posterior location for anchor blades on the cage implant to engage the vertebral bodies. Inserter 202 is used to introduce cage implant 204 with anchor blades into the disc space to an appropriate depth so that the blades will be deployed into slots created by the scoring element of implant trial 104, as will be described.

Figure 2:
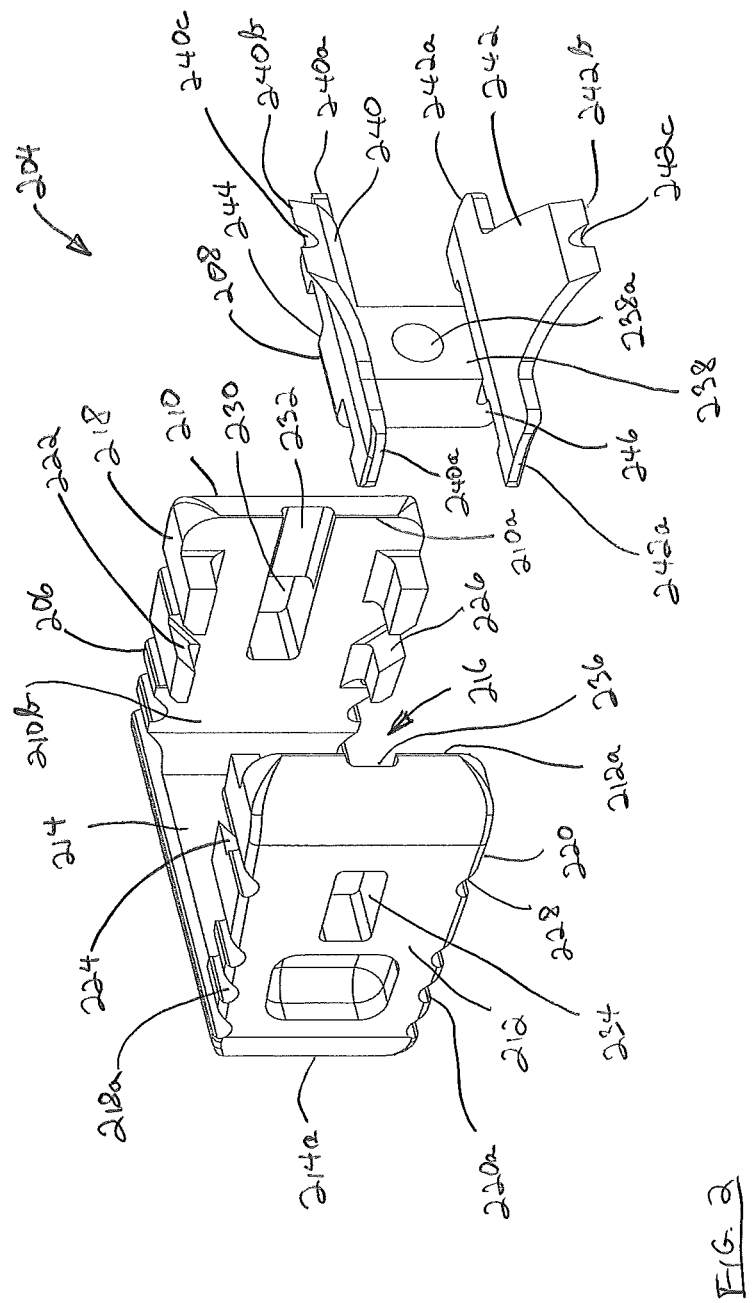
FIG. 2 is an exploded top perspective view of an interbody fusion cage implant for use in the system of FIG. 1, comprising an interbody fusion cage and an anchor plate.

Turning now to FIGS. 2-6, details of interbody cage implant 204 are first described. Cage implant 204 as shown in FIG. 2 comprises a cage 206 and anchor plate 208. Cage 206 is formed of size and configuration for insertion into the disc space between opposing vertebral bodies. Cage 206 comprises a pair of spaced opposing side walls 210 and 212 and a rear wall 214 therebetween. Side walls 210, 212 and the rear wall 214 formed a generally U-shaped open cavity 216 for receipt of anchor plate 208 and bone graft. An exterior surface 214a of rear wall 214 defines a distal surface of cage 206 while the exterior surfaces at the free ends 210a and 212a of sidewalls 210 and 212 define a proximal surface at the opposite end of cage 206. Cage 206 includes a top surface 218 and a bottom surface 220. Top surface 218 and bottom surface 220 may be formed to each include respective anti-expulsion features 218a, 220a, such as teeth, ratchetings or other suitably abrasive surfaces. In one arrangement, top surface 218 and bottom surface 220 may be formed to taper downwardly toward distal surface 214a defining cage 206 to have a lordotic configuration as well as to facilitate entry of cage 206 into the disc space. Each side wall 210 and 212 has a respective slot 222 and 224 extending at an angle through top surface 218. Each side wall 210 and 212 further includes a respective slot 226 and 228 extending at an angle through bottom surface 220. Each of top slots 222, 224 and bottom slots 226, 228 communicates with open cavity 216. Sidewall 210 includes an opening 230 extending therethrough and a channel 232 extending into interior surface 210b of sidewall 210. Sidewall 212 includes an opening 234 extending therethrough and a channel 236 extending into an interior surface of sidewall 212. Openings 230, 234 and channels 232, 236 facilitate the releasable connection of inserter 102 thereto, as will be described. In one particular arrangement, cage 206 is formed of polyetheretherketone (PEEK), although cage 206 may be formed of other suitable biocompatible materials, such as, e.g., titanium, stainless steel or carbon fiber PEEK.

Still referring to FIG. 2, anchor plate 208 comprises a base 238 supporting an upper blade 240 and a lower blade 242. Base 238 has a threaded opening 238a therethrough for threaded connection to inserter 102, as will be described. Upper blade 240 is attached to base 238 by a plastically deformable joint 244 and lower blade 242 is attached to base 238 by a plastically deformable joint 246. Upper blade 240 and lower blade 242 have elastic, spring properties. Upper blade 240 includes a pair of laterally spaced wings 240a and lower blade 242 includes a pair of laterally spaced wings 242a. Wings 240a are sized and configured to extend into respective top slots 222 and 224 extending through top surface 218 and wings 242a are sized and configured to extend into respective bottom slots 226 and 228 extending through bottom surface 220 when the blades 240 and 242 are deployed, as will be described. Upper blade 240 includes a penetration tip 240b at its distal free end and lower blade 242 includes a penetration tip 242b at its distal free end. Penetration tips 240b and 242b are each formed to be sufficiently sharp to penetrate into the endplates of adjacent vertebral bodies. Each respective tip 240b and 242b may be provided with a notch 240c and 242c to facilitate retention of each blade in a respective vertebral endplate. In one particular arrangement, anchor plate 208 is formed of titanium, although anchor plate 208 may be formed of other suitable biocompatible materials, such as, e.g., stainless steel.

Figure 3:
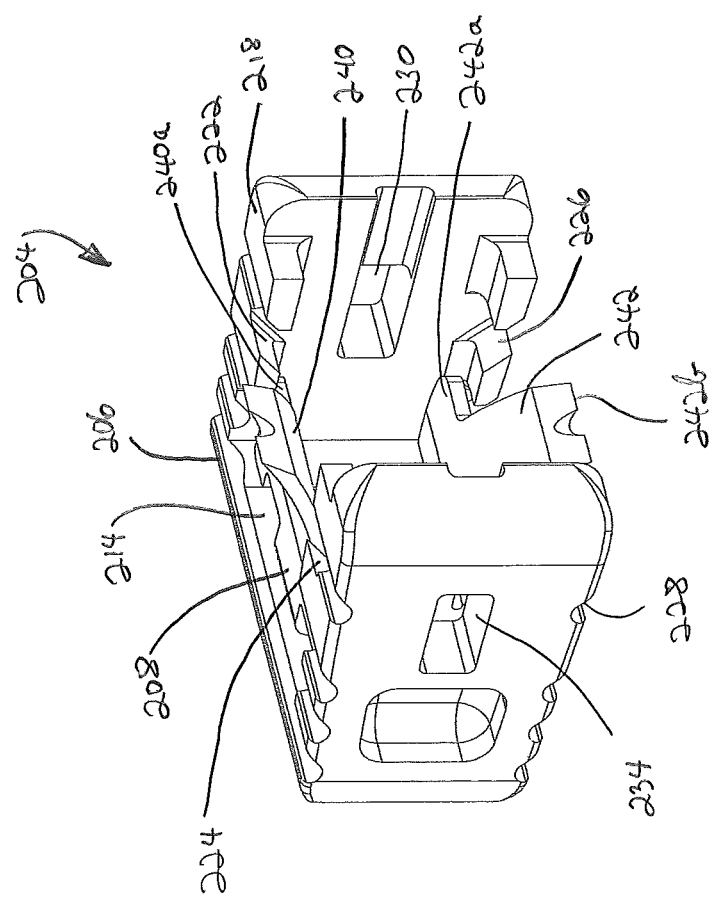
FIG. 3 is a top perspective view of the assembled cage implant of FIG. 2 with the anchor plate being disposed in a first non-deployed position.

FIGS. 3 and 4 show anchor plate 208 disposed in cage 206 in a non-deployed first position. In this stage, anchor plate 208 is supported by cage 206 and is disposed between distal surface 214a and proximal surface 210a, 212a with base 238 being situated against or closely adjacent to rear wall 214. Wings 240a of upper blade 240 are spaced distally of and not extending into slots 222 and 224 of cage 206, as depicted in FIG. 3. Similarly wings 242a of lower blade 242 are spaced distally of and not extending into slots 226 and 228 of cage 206. In this position, blade penetration tips 240b and 242b may extend slightly above and below respective top and bottom surfaces 218 and 220, as illustrated in FIG. 4. It should be appreciated, however, that such blade penetration tips 240b and 242b may also lie substantially flush with or within respective top and bottom surfaces 218 and bottom surface 220. The location of the anchor blades 240, 242 in the non-deployed position relative to the cage proximal surface 210a, 212a is used in conjunction with the disc preparation instrument 100, as will be described, to create a scored location in the vertebral endplates that corresponds to entry locations for the penetration tips 240b, 242b of the anchor blades 240, 242 upon deployment. In this regard, penetration tips 240b, 242b are spaced from cage proximal end 210a, 212a by a predetermined, set spacing, $S_1$ as shown in FIG. 4. It should be understood that other locations on cage implant 204, such as, for example the spacing of top slots 222, 224 or bottom slots 226, 228 from cage proximal surface 210a. 212a may also be used as reference locations for correlation with the scoring function of the disc preparation instrument 100.

Upper blade 240 is deployed upon movement of anchor plate 208 in the proximal direction by inserter 202, as will be described. Upon such proximal movement of anchor plate 208, upper blade 240 is caused by inserter 202 to deploy by moving arcuately in an upward direction such that wings 240a extend into and are constrained by the surfaces defining upper slots 222 and 224. During such movement of anchor plate 208, lower blade 242 is caused to deploy by inserter 202 by moving arcuately in a downward direction such that wings 242a extend into and are constrained by the surfaces defining lower slots 226 and 228. The positions of upper blade 240 and lower blade 242 in the second deployed position are illustrated in FIGS. 5 and 6. Further details of an anchor plate with deployable anchor blades deployed by an implant inserter are described in the '051 Application, incorporated herein by reference in its entirety.

Figure 7:
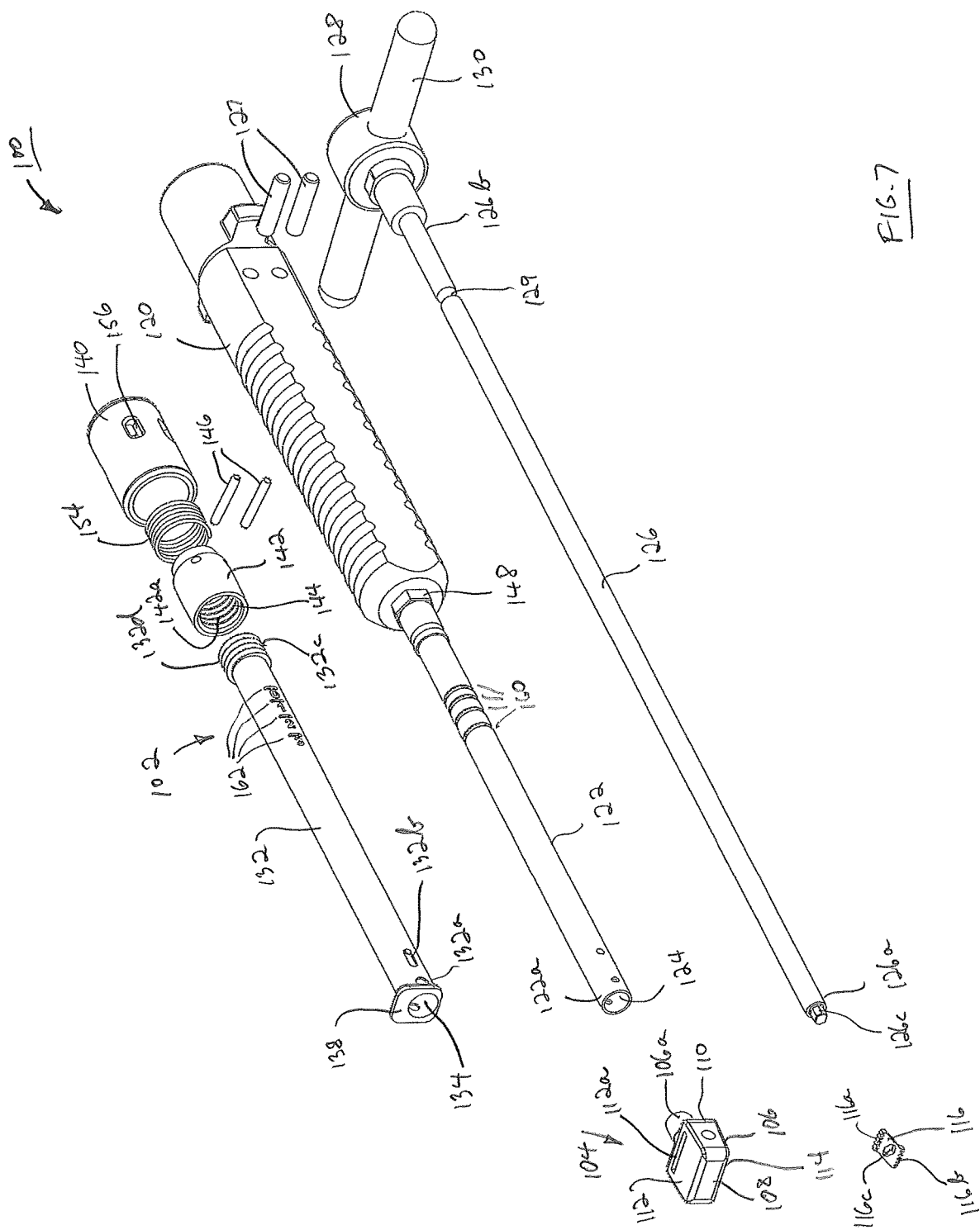
FIG. 7 is a top perspective exploded view of the disc preparation instrument of the system shown in FIG. 1.
Figure 8:
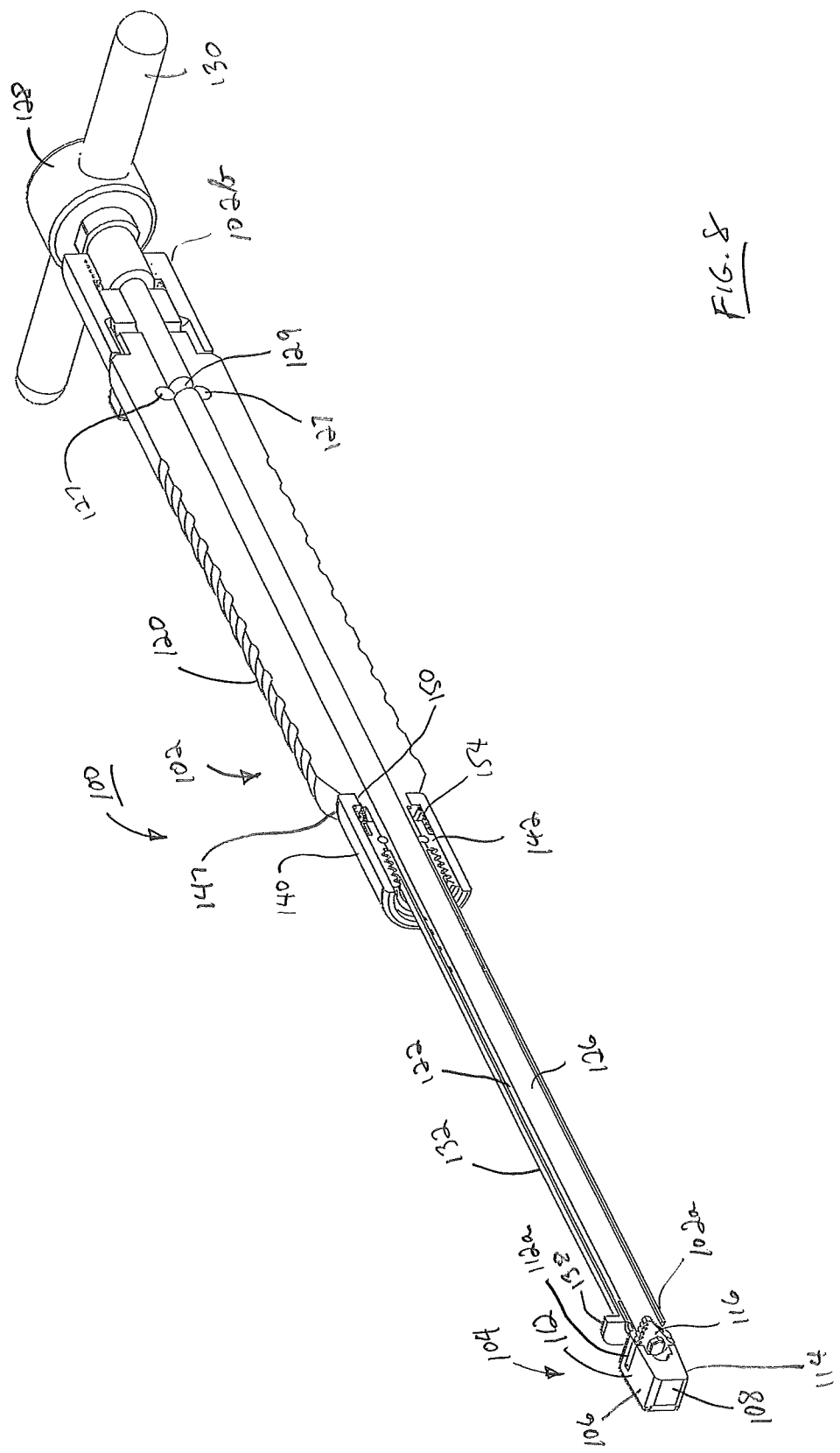
FIG. 8 is a perspective partially sectioned longitudinal view of the disc preparation instrument of FIG. 7.

Turning now to FIGS. 7-11, the details of disc preparation instrument 100 are described. Disc preparation instrument 100 comprises elongate handle 102 supporting a trial device 104, as noted hereinabove. Body 106 has a distal surface 108, a proximal surface 110, a top surface 112 and a bottom surface 114. Top surface 112 has a top opening 112a and bottom surface 114 has a bottom opening (not shown) similar to top opening 112a. Body 106 supports a rotatably movable scoring element 116 disposed between distal surface 108 and proximal surface 110 and having a first upper portion 116a and a second lower portion 116b. Scoring element 116 is selectively movable from a first position wherein first portion 116a and second portion 116b are both disposed interiorly of trial device 104 as shown in FIG. 8 to a second position shown in FIG. 9 wherein first portion 116a extends exteriorly of body 106 through top opening 112a and second portion 116b extends exteriorly of body 106 through bottom opening. First portion 116a and second portion 116b each includes in a particular aspect a rasped scoring surface along the edges thereof to facilitate scoring of the surfaces of vertebral endplates, although other abrasive surfaces may also be used. While scoring element 116 in the arrangement shown is rotatable it should be appreciated that first portion 116a and second portion 116b may also, in an alternative approach, be supported to move linearly from the first position to the second position. Trial device 104 may be used for the dual purpose of scoring and trialing, but could be used only for scoring. In the dual configuration, trial body 106 is of size and configuration approximating the size and configuration of cage implant 204 for insertion into the disc space. In this regard, trial body 106 may be formed to taper downwardly toward distal surface 108 defining trial body 106 to have a lordotic configuration, as illustrated in FIGS. 7 and 8, in the same manner as cage implant 204.

With reference still to FIGS. 7-8, elongate handle 102 has a distal end 102a and a proximal end 102b, trial device 104 being supported at distal end 102a. Handle 102 comprises a handle grip 120 including an inner sleeve 122 affixed thereto for joint movement. A lumen 124 extends fully through handle grip 120 and inner sleeve 122. The distal end 122a of inner sleeve 122 is suitably fixedly attached in one arrangement to an attachment ring 106a provided at the proximal surface 110 of trial body 106. It should be appreciated that trial body 106 may be releasably attached to inner sleeve 122 such that a kit of differently sized trial bodies 106 may be provided in a kit for selective use with inner sleeve 122. An elongate shaft 126 having a distal end 126a and a proximal end 126b extends within lumen 124 of handle 102 through handle grip 120 and inner sleeve 122 and is rotatable but not translatable within lumen 124. Translation of shaft 126 relative to handle grip 120 is prevented by pins 127 disposed in a groove 129 extending around the circumference of shaft 126. Distal end 126a includes an engagement feature 126c for extending into trial body 106 and engaging scoring element 116. In one particular arrangement, engagement feature 106c is a multi-faceted drive sized and configured to engage with a complementary sized and configured opening 116c formed in scoring element 116. Shaft 126 has an actuator 128 at proximal end 126b, actuator 128 being operable to rotate shaft 126 and thereby scoring element 116 at the distal end 126a thereof. In one particular arrangement actuator 128 comprises a rotatable T-handle 130 for rotating shaft 126 and scoring element 116. T-handle 130 may be oriented with respect to scoring element 116 in a manner to visually determine when scoring element 116 is in the first position or the second position, as described above. For example, when T-handle 130 is oriented in a generally horizontal position scoring element 116 may be in the first position whereby first portion 116a and second portion 116b are disposed interiorly of trial device 104. When T-handle 130 is oriented in a generally vertical position after having been rotated approximately 90 degrees to the second position, first portion 116a of scoring element 116 extends exteriorly of body 106 through top opening 112a and second portion 116b extends exteriorly of body 106 through bottom opening, as shown in FIG. 9.

The location of the scoring element 116 relative to the trial body proximal surface 110 is used in conjunction with the inserter assembly 200, described hereinabove, to create a scored location in the vertebral endplates that corresponds to entry locations for the penetration tips 240b, 242b of the anchor blades 240, 242 upon deployment. In this regard, scoring element 116, in particular its distal surface 116c, is spaced from trial body proximal end 110 by a predetermined, set spacing, $S_2$ as shown in FIG. 9. Spacing, $S_2$ is predetermined to be approximately the same dimension as spacing, $S_1$, namely, the spacing penetration tips 240b, 242b of anchor blades 240, 242 are spaced from cage proximal end 210a, 212a. As such, positioning the proximal surfaces of the trial body 106 and cage implant at the same location in the disc space will align the anchor blade penetration tips 240b, 242b with a scored location formed in the endplates of opposing vertebral bodies by scoring element first and second portions 116a, 116b. It should be understood that other locations on trial body 106, such as, for example the proximal surface 116d of scoring element 116 may also be used as a reference location for correlation with the anchor blade penetration tips 240b, 242b.

Figure 9:
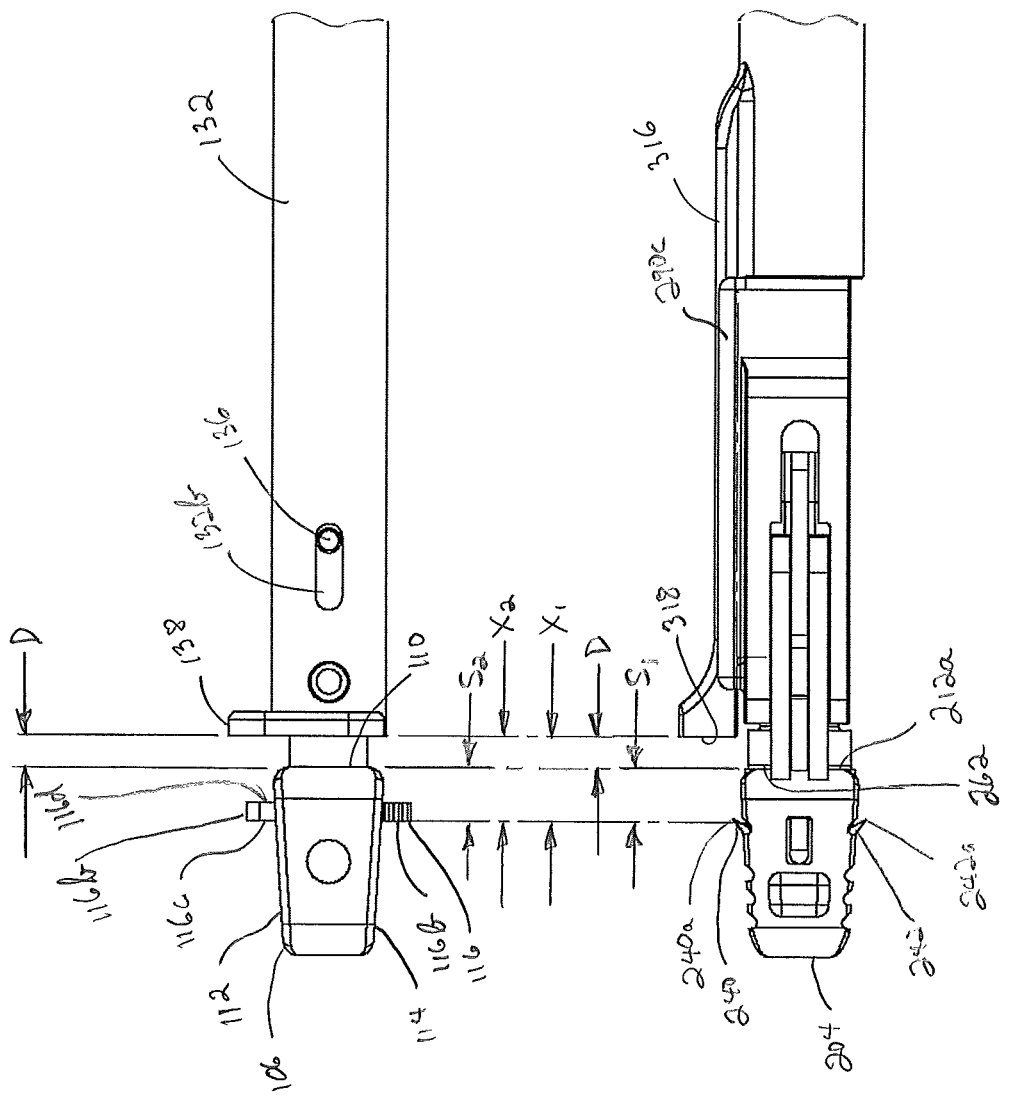
FIG. 9 is a side elevational view of the distal ends of the disc preparation instrument and the inserter assembly of the system of FIG. 1 showing the spacing between the vertebral endplate scoring element and the adjustable depth stop of the disc preparation instrument and the corresponding spacing between the anchor plate penetration tips of the cage implant and the adjustable shoulder of the inserter assembly.

Referring further to FIGS. 7-9 and also to FIG. 10, handle 102 further comprises an elongate outer sleeve 132 supported by inner sleeve 122 which extends through a lumen 134 extending through outer sleeve 132. Outer sleeve 132 is coupled to inner sleeve 122 by a pin 136 through a slot 132b as shown in FIG. 9 that allows translation of outer sleeve 132 relative to inner sleeve 122, but not rotation. The extent of relative axial movement is controlled by the axial length of slot 132b. Outer sleeve 132 supports an adjustably movable depth stop 138 at a distal end 132a of outer sleeve 132. Depth stop 138 is sized and configured to engage an exterior surface of a vertebra when trial device 104 is disposed in the intradiscal space, as will be described.

Handle 102 includes at the proximal end 132c of outer sleeve 132 an adjustment knob 140 to axially move outer sleeve 132 and thereby depth stop 138 along inner sleeve 122. Outer sleeve 132 has at its proximal end 132c an externally threaded extent 132d. A collar 142 is disposed within adjustment knob 140, collar 142 having an opening 142a with internal threads 144. Internal threads 144 threadably engage external threads 132d at the proximal end 132c of outer sleeve 132. Adjustment knob 140 is pinned to collar 142 by pins 146 that prevent rotation of adjustment knob 140 relative to collar 142, but allow translation. Thus, when adjustment knob 140 is rotated in a clockwise motion when handle grip 120 is held by a user, collar 142 will likewise be rotated causing axial movement of outer sleeve 132 and depth stop 138 thereon in the distal direction on inner sleeve 122 as result of the threaded coupling between external threads 132d and internal threads 144.

In a particular arrangement a releasable lock 147 is provided between adjustment knob 140 and handle grip 120, as depicted in FIGS. 7 and 8, to prevent inadvertent axial movement of outer sleeve 132 relative to inner sleeve 122. In this arrangement, at the interface of handle grip 120 and inner sleeve 122, a locking surface 148, such as a hex surface, is formed. An opening 140a as shown in FIG. 10 having a complementary hex engagement is formed on adjustment knob 140. A compression spring 154 is captured between an interior surface 152 of adjustment knob 140 and collar 142. A slot 156 is formed through adjustment knob 140 to receive at least one pin 146, slot 156 allowing a limited amount of axial movement of pin 146 therewithin. In the normal state, spring 154 applies a force against interior surface 152 of adjustment knob 140 causing hex engagement surface 140a to couple with hex locking surface 148. In this state, relative rotation between adjustment knob 140 and inner sleeve 122 is prevented. Applying a manual force to adjustment knob 140 in the distal direction to overcome the bias of spring 154 will cause limited distal movement of adjustment knob 140 as pin 146 axially moves within adjustment knob slot 156. Such limited axial movement is sufficient to cause separation of adjustment knob 140 from locking surface 148, thereby permitting rotation of adjustment knob 140 and axial movement of outer sleeve 132 and depth stop 138 relative to inner sleeve 122. Release of such manual force allows adjustment knob 140 to spring back under the bias of spring 154 in the proximal direction to engage locking surface 148.

Turning now to FIGS. 10-11, handle 102 further comprises an indicator device 158 operable with the axial movement of outer sleeve 132 along inner sleeve 122 to provide a visual indication of a plurality of selectable distances that depth stop 138 may move relative to trial device 104, as will be described. In a particular arrangement, inner sleeve 122 is provided with a plurality of markings 160 or other suitable indicia, as shown in FIGS. 10 and 11. Such markings may be in the form of stripes or bands formed around the circumference of inner sleeve 122. Each marking 160 is representative of a different distance that depth stop 138 is spaced from a location on the trial body 106. Such location on the trial body 106 may be its proximal surface 110. Each distance, D, for example, that the depth stop 138 is selectively spaced from the proximal surface 110 of trial body 106 is indicated by a different marking 160 that will be visually observable through one of an equal number of windows 162 formed through outer sleeve 132. Windows 162 are axially spaced from each other along outer sleeve 132 at approximately the same distances, with each window representing a change in distance, D of approximately 1 mm. Markings 160 are spaced from each other along inner sleeve 122 at different distances that are ordered by timing in dimensional increments, such as in increments of millimeters. As such, when outer sleeve 132 and depth stop 138 are axially moved relative to inner sleeve 122 and hence trial body 106 affixed thereto, windows 162 will axially move relative to markings 160 and only one marking 160 will appear through one window 162 at a time. Accordingly, in the arrangement shown in FIGS. 10 and 11, indictor device 158 includes four windows, denoted a "0", "1", "2," and "3". The spacing in indicator device 158 from marking "0" to marking "1" is 1 mm greater than the spacing between windows 162. The spacing from marking "1" to marking "2" is 2 mm greater than the spacing between windows 162. The spacing from marking "2" to marking "3" is 3 mm greater than the spacing between windows 162. The "0" window may indicate a distance, D of approximately 2 mm, the "1" window a distance, D of approximately 3 mm, the "2" window a distance, D of approximately 4 mm, and the "3" window a distance, D of approximately 5 mm. As illustrated in FIG. 11, marking 160 appears in window "2", indicating that depth stop 138 is spaced a distance, D of approximately 4 mm from trial body proximal surface 110.

Turning now primarily to FIGS. 12 and 13, the details of elongate inserter 202 of inserter assembly 200 are described with the details of cage implant 204 having been described above. Elongate inserter 202 has a distal end 202a and a proximal end 202b, cage implant 204 being supported at distal end 202a. Inserter 202 comprises an inserter grip 250 including an inner shaft 252 affixed thereto. A lumen 254 extends fully through inserter grip 250 and inner shaft 252. The distal end 252a of inner shaft 252 includes a cage implant support 256 suitably affixed to inner shaft 252 by a clip 258 or other suitable attachment device. Implant support 256 includes a pair of axially extending laterally spaced insertion tips 260. Insertion tips 260 project axially beyond contact surface 262 and are sized and configured to enter opening 216 of cage implant 204 with one tip 260 being situated between base 238 of anchor plate 208 and one sidewall 210 and the other tip 260 between base 238 and the other sidewall 212. Laterally outwardly of insertion tips 260 implant support 256 includes a pair of flexible hooks 264 at the free end thereof. During insertion of tips 260 into cage implant opening 216, flexible hooks 264 will flex toward each other and ride within channels 232, 236 (FIG. 2) in respective sidewalls 210, 212 until hooks 264 reach openings 230, 234 in sidewalls, at which point hooks 264 snap back in a manner to releasably attach implant support and thereby inserter 202 to cage implant 204. Upon releasable attachment of hooks 264 to cage implant 204, the distal ends 260a of each tip 260 lie against or closely near the interior surface of rear wall 214 while contact surface 262 lies against or closely near proximal surface 210a, 212a of cage implant 204 (See FIG. 9). Cage implant support 256 further includes a pair of elongate slots 266 extending therethrough, the function of which will be described.

Proximal end 252b of inner shaft 252 is affixed to inserter grip 250 by a pin 268 which prevents any relative rotation or translation between inner shaft 252 and inserter grip 250. Elongate inserter 202 includes a deployment knob 270 threadably supported at the proximal end of inserter grip 250. Deployment knob 270 includes external threads 270a for threaded engagement with internal threads 250a interiorly of inserter grip 250, as shown in FIG. 13. Threads 270a and 250a are left-handed threads, meaning that upon clockwise rotation of deployment knob 270 relative to inserter grip 250, deployment knob will translate axially in the proximal direction. Deployment knob 270 further includes a lumen 272 extending therethrough in axial communication with lumen 254 extending through inserter grip 250 and inner sleeve 252. Deployment knob 270 is pinned to inserter grip 250 by pins 274 that reside in a groove 276 in deployment knob 270, grove 276 allowing a limited amount of axial translation and preventing deployment knob 270 from being removed from inserter grip 250.

An elongate pull rod 278 extends through lumen 254 of inserter grip 250 and inner sleeve 122 and through lumen 272 of deployment knob 270. Distal end 278a of pull rod 278 includes threads 280 for releasable threaded engagement with the threads of threaded opening 238a in anchor plate 208. A pull rod knob 282 is fixedly attached to the proximal end 278b of pull rod 278. Pull rod 278 is attached to anchor plate 208 by inserting distal end 278a through deployment knob lumen 272 and through lumen 254 of inserter grip 250 and inner sleeve 252 until threads 280 enter threaded opening 238a of anchor plate 208. Pull rod knob 282 is rotated in a clockwise motion to thread pull rod threads 280 into threaded anchor plate opening 238a. Anchor plate 208 is moved to deploy anchor blades 240 and 242 upon rotation of deployment knob 270 in a clockwise motion. Due to the left-handed threaded connection, deployment knob 270 will move with clockwise rotation in the proximal direction until proximally facing surface 270b on deployment knob 270 contacts distally facing surface 282a on pull rod knob 282. Clockwise rotation of deployment knob 270 will draw pull rod 278 in the proximal direction, deploying anchor blades 240 and 242 to the deployed second position as described above and shown in FIG. 6. When pins 274 engage the distal side of groove 276 proximal motion of deployment knob 270 is complete and anchor blades 240 and 241 are fully deployed.

Elongate inserter 202 further includes an inner sleeve 284 having a lumen 286 extending fully therethrough and through which inner shaft 252 is received. The distal end 284a of inner sleeve 284 is suitably fixedly attached to a shoulder support 290 such that shoulder support 290 is movable jointly with inner sleeve 284. Shoulder support 290 includes a channel 292 within which cage implant support 256 is slidably received. Shoulder support 290 has pair of pins 294 extending respectively through a pair of top openings 290a and a pair of bottom openings 290b. Pins 294 also extend through slots 266 extending through cage implant support 256. The elongated extent of slots 266 allow shoulder support 290 to slide axially in the proximal direction by a limited amount relative to cage implant support 256. During such proximal sliding movement, pins 294 contact the flexible hooks 264 at the ends thereof causing hooks 264 to compress medially laterally toward each other in a manner to move hooks 264 out from cage implant openings 230 and 234 so that cage implant support 256 and thereby elongate inserter 202 may be separated from cage implant 204 when a surgical procedure is complete.

The opposite proximal end 284b of inner sleeve 284 is received though a lumen 296 extending fully through an outer sleeve 298 slidably supported on inner sleeve 284. Proximal end 284b of inner sleeve 284 extends into a lumen 302 extending fully through a depth controller 300, proximal end 284b being fixedly attached to depth controller 300 such that inner sleeve 284 and depth controller 300 are movable jointly. External threads 304 are provided about the outer circumference of depth controller 300. Proximal end 300a of depth controller 300 has a reduced diameter that is received through a lumen 306 extending fully through a rotatable adjustment member 308. Lumen 306 includes internal threads 310 extending circumferentially thereabout. Proximal end 300a of controller 300 extends into a lumen 312 of a hook actuator 314 having a lumen 312 extending fully therethrough. Proximal end 300a of depth controller 300 is fixedly attached to hook actuator 314 such that inner sleeve 284, depth controller 300 and hook actuator 314 are all movable jointly.

Referring still to FIGS. 12 and 13, outer sleeve 298 has a distal end 298a and a proximal end 298b. Distal end 298a includes an axially extending arm 316 affixed thereto and terminating at its distal end in a shoulder 318. Shoulder 318 is axially movable relative to shoulder support 290 and is sized and configured to engage an exterior surface of a vertebra when cage implant 204 is disposed in the intradiscal space, as will be described. As such, shoulder 318 serves as an adjustable depth stop for use in aligning blade penetration tips 240b, 242b of cage implant 204 with a scored location formed on endplates of opposing vertebral bodies by scoring element 116 of disc preparation instrument 100. Arm 316 is sized and configured to be slidably received in track 290b formed on an upper surface of shoulder support 290, as depicted in FIG. 12. Track 290b is defined by a pair of laterally spaced rails 290c. Rails 290c permit axial movement of arm in track 290b, but substantially prevent rotational movement between inner sleeve 284 and outer sleeve 298.

Proximal end 298b of outer sleeve 298 has a pair of axially spaced annular plates 320 defining a grove 322 therebetween, as shown in FIG. 12. Outer sleeve 298 is attached to depth adjustment member 308 by a pair of pins 324 extending through openings 308a in adjustment member 308 and residing in groove 322. As such, adjustment member 308 may rotate relative to outer sleeve 298, but not translate relative thereto. In assembly as shown in FIG. 13, external threads 304 of depth controller 300 threadably engage internal threads 310 on adjustment member 308. Rotation of adjustment member 308 in a clockwise motion when inserter grip 250 is held in a stationary position will cause outer sleeve 298 and hence shoulder 318 affixed thereto to move axially in the distal direction toward cage implant 204. Rotation of adjustment member 308 in a counterclockwise motion will cause outer sleeve 298 and shoulder 318 to move axially in the proximal direction away from cage implant 204.

As described hereinabove, shoulder support 290 is configured to slide axially in the proximal direction by a limited amount relative to cage implant support 256 in a manner to cause hooks 264 to compress and allow elongate inserter 202 to be separated from cage implant 204 upon completion of a surgical procedure. Such movement of shoulder support 290 in the proximal direction is effected by movement of hook actuator 314. As explained above, hook actuator 314 is fixedly attached to depth controller 300, which in turn is fixedly attached to inner sleeve 284, and which in turn is fixedly attached to shoulder support 290. Axial movement of hook actuator 314 thus axially moves the entire subassembly of hook actuator 314, depth controller 300, inner sleeve 284 and shoulder support 290 axially on inner shaft 252. Furthermore, as rotatable adjustment member 308 is threadably engaged with depth controller 300 and outer sleeve 298 is axially coupled to rotatable adjustment member 308, upon axial movement of hook actuator, in addition to axial movement of the subassembly, adjustment member 308 and outer sleeve 298 with shoulder 318 thereon will also axially move with the subassembly.

In order to prevent inadvertent movement particularly of shoulder 318 relative to cage implant 204, a lock is provided. In this arrangement as shown in FIGS. 12 and 13, a lock 326 comprises a rotatable lock knob 328 configured to selectively engage portions of hook actuator 314 in a manner to allow and prevent axial movement of the hook actuator, and hence inadvertent movement of shoulder 318. Lock knob 328 supports a helical compression spring 330 at one end, the free end 330a of spring 330 being sized and configured to engage a proximally facing contact surface 314a on hook actuator 314. A pair of arcuate slots 328a is formed into lock knob 328, slots 328a in one arrangement being approximately diametrically opposed. Lock knob 328 is suitably supported at the distal end 250b of inserter grip 250 for rotational but not translational movement. Hook actuator 314 includes a pair of complementary arcuate tabs 314b projecting proximally therefrom, tabs 314b being sized and configured to enter knob slots 328a. In normal use, tabs 314b contact lock knob 328 at the surfaces 328b between slots 328a thereby preventing axial movement of hook actuator 314. Upon rotation of lock knob 328, tabs 314b may be aligned with knob slots 328a, allowing tabs 314b to enter slots 328a and thereby allow axial movement of hook actuator 314 in the proximal direction. Such movement is achieved by manually compressing spring 330 an amount to allow shoulder support 290 to move proximally to cause pins 294 on implant support 256 to depress hooks 264 for removal of elongate inserter 202 from cage implant 204. Upon release of the manual force on hook actuator 314, hook actuator 314 will return to its original position under the normal bias of spring 330 whereby lock knob 328 may be rotated to position tabs 314b between slots 328a on surfaces 328b to prevent further axial movement.

With reference still to FIGS. 12 and 13, inserter 202 further comprises an indicator device 332 substantially the same as indicator device 158 on handle 102 of disc preparation device 100, described above. As such, indicator device 332 is operable with the axial movement of outer sleeve 298 along inner sleeve 284 to provide a visual indication of a plurality of selectable distances that shoulder 318 may move relative to cage implant 204. In a particular arrangement, inner sleeve 284 is provided with a plurality of markings 334 or other suitable indicia, as shown in FIG. 12. Such markings 334 may be in the form of stripes or bands formed around inner sleeve 284. Each marking 334 is representative of a different distance that shoulder 318 is spaced from a location on the cage implant 204 and will be visually observable through one of an equal number of windows 336 formed through outer sleeve 298. Such location on the cage implant 204 may be its proximal surface 210a, 212a. With indicator device 332 being substantially the same as indictor device 158, the distance, D that the depth stop 138 is spaced from the proximal surface 110 of trial body 106, as determined by a reading on indicator device 158, may be transferred to indicator device 332 of inserter assembly 200. As such, transferred distance, D for inserter assembly 200 would determine the spacing between shoulder 318 and proximal surface 210a, 212a of cage implant 204, as shown in FIG. 9. For example, a reading with a marking 160 appearing in window "2" of indicator device 158 would be transferred to indicator device 332 by rotating adjustment member 308 to move outer member 298 relative to inner member 284 until a marking 334 appears in the "2" window. Thus, in the example provided above, the distance, D between shoulder 318 and proximal surface 210a, 212a of cage implant 204 would be approximately 4 mm, the same as the distance between depth stop 138 and the proximal surface 110 of trial body 106. Thus, the spacing, $X_1$ between anchor penetration tips 240b, 242b and shoulder 318 of inserter assembly 200 is $S_1+D$ and the spacing, $X_2$ between the scoring element 116 and the depth stop 138 of disc preparation instrument 100 is $S_2+D$. With $S_1=S_2$, then $S_1+D=S_2+D$ and $X_1=X_2$. Accordingly, the precise location of the scored location formed by scoring element 116 can be ascertained for positioning and penetration by anchor penetration tips 240b, 242b by transferring the distance, D from the disc preparation instrument 100 to the inserter assembly 200.

Figure 14:
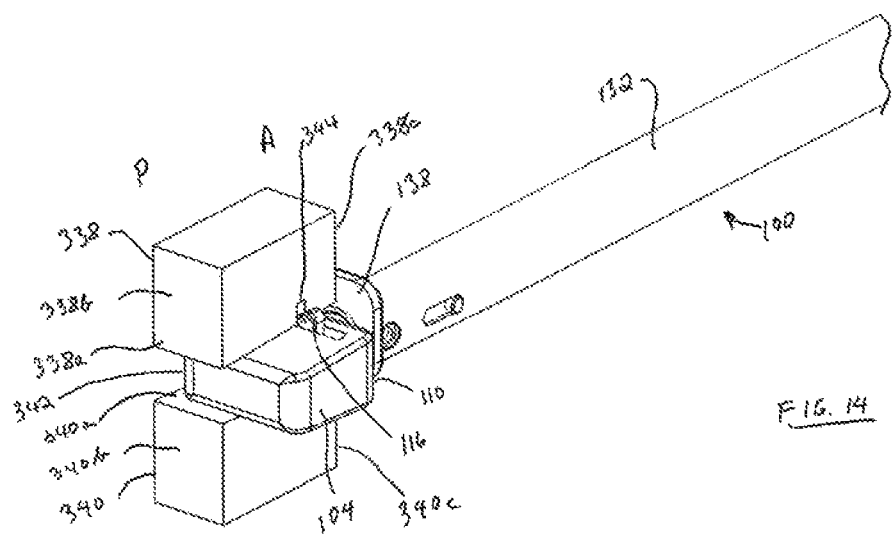
FIG. 14 is a perspective view showing the distal end of the disc preparation instrument with the trial device being disposed in an intradiscal space between two opposing vertebral bodies of a spine, the vertebral bodies being partially sectioned for clarity, the scoring element of the trial device being shown in a second position forming a scored location in the endplates of the vertebral bodies.

Having described the system 10 comprising disc preparation instrument 100 and inserter assembly 200, a method for use in an interbody fusion procedure is described, with particular reference to FIGS. 14-16. In one particular approach, system 10 is used to fuse together a superior vertebra 338 and an inferior vertebra 340 in the cervical region of the spine in a procedure known as a Smith-Robinson approach. It should be appreciated, however, that system 10 may also be used in interbody fusion procedures in other regions of the spine. Superior vertebra 338 includes an inferior endplate 338a, a vertebral body 338b, and an exterior anterior surface 338c. Inferior vertebra 340 includes a superior endplate 340a, a vertebral body 340b and an exterior anterior surface 340c. Superior endplate 338a and inferior endplate 340a define an intradiscal space 342 therebetween. Endplates 338 a, 340a consist primarily of relatively hard bony/cartilaginous material that is often difficult to penetrate for fixing fusion implants for interbody fusion purposes. In the cervical spine procedure, access to the spine is often provided by forming an incision through the anterior portion of the patient's neck to expose superior and inferior vertebrae 338, 340. As such, exterior surfaces 338c, 340c of superior vertebra 338 and inferior vertebra 340, respectively, are anterior surfaces. A suitable discectomy is performed to provide an appropriate disc space 342 for receipt of cage implant 204. It should be understood that access may be provided in other approaches, such as posterior or lateral depending upon the nature of the procedure and the surgeon's preference.

Disc preparation instrument 100 is used to suitably prepare opposing vertebral endplates 338a, 340a for receipt of cage implant 204. Handle 120 of disc preparation instrument 100 is used to introduce trial device 104 into the disc space 342 using suitable imaging techniques, such as fluoroscopy. Such imaging includes a side view from the lateral perspective so that the depth of trial device 104 along the anterior-posterior (A/P) direction may be observed. Upon determination of an appropriate depth of trial device 104 in the A/P direction, adjustment knob 142 is released from lock 147 by applying a manual force to adjustment knob 140 in the distal direction to overcoming the bias of spring 154. Adjustment knob 140 is rotated in a clockwise motion while adjustment knob 140 is separated from lock 147 to move outer sleeve 132 until depth stop 138 contacts exterior anterior surface 338c of superior vertebra 338. It should be understood that depth stop 138 in the alternative may also be configured on disc preparation instrument 100 to contact exterior anterior surface 340c of inferior vertebra 340. The manual force on adjustment knob 140 is released thereby causing adjustment knob 140 to reengage with lock 147 to thereby fix the position of adjustment stop 138 against anterior surface 338c. Indicator device 158 is observed to determine through which window 162, such as the "2" window, a marking 160 appears, with such window 162 being suitably noted. If marking 160 is not evident through any one window 162, the depth stop 138 of trial device 104 may be adjusted in the A/P direction by rotating adjustment knob 140 until a marking 160 appears through a particular window 162. This establishes the distance, D, as described hereinabove, that proximal surface 110 of trial device 104 is spaced in disc space 342 from depth stop 138 and hence exterior anterior surface 338c of vertebra 338. It further establishes spacing, $X_2$ between the scoring element 116 and the depth stop 138 of disc preparation instrument 100.

Vertebral endplates 338a, 340a are then scored with disc preparation instrument 100. Scoring is effected by the rotation of T-handle 130 which rotates scoring element 116 from the first position to the second position, as depicted in FIG. 14. Such rotation causes the abrasive edges of first portion 116a and second portion 116b of scoring element 116 to cut a slot 344 into endplates 338a, 340a. Complete penetration of slots 344 into the bony/cartilaginous endplates 338a, 340a may not be necessary as slots 344 provide a weakened, secured location to facilitate entrance of anchor plates 240, 242 on cage implant 204. T-handle 130 may be actuated several times if necessary in order to suitably form scored location 344, with proper penetration of scoring element 116 being achieved when T-handle 130 is in a substantially vertical orientation. Upon achievement of endplate scoring, T-handle 130 is rotated to the horizontal orientation to thereby rotate scoring element 116 back to the first position wherein scoring element 116 lies fully contained within trial device 104. At this point in the procedure, trial device 104 is removed by manually pulling handle 120 in a proximal direction.

As described hereinabove, trial body 106 of trial device 104 is of size and configuration approximating the size and configuration of cage implant 204 for insertion into the disc space. As such, trial device 104 may also be used to assess a space between two vertebrae. Thus, trial device 104 may serve two purposes—to prepare one or more endplate surfaces for receiving cage implant 204 and to test a size for the selection of an appropriately sized cage implant 204. In this regard, a plurality of disc preparation instruments 100, each having a trial device 104 of different heights may be provided in a kit. Alternatively, a series of differently sized trial devices 104 may be provided in the kit for separate releasable attachment to a single elongate handle 102. In either case, a variety of trial devices 104 may be made available for use in assessing the size of the disc space 342 for selection of an appropriately sized cage implant 204. A plurality of differently sized cage implants 204 may be provided in the kit to allow for selection based upon the assessment of disc space 342.

Upon determination of the proper size of disc space 342 and selection of an appropriately sized cage implant 204, the selected cage implant 204 is releasably attached to elongate inserter 202 of inserter assembly 200. Such attachment is effected by insertion of tips 260 of cage implant support 256 into cage implant opening 216 until flexible hooks 264 engage openings 230, 234 in sidewalls 210, 212, as described above. Pull rod 278 is then attached to anchor plate 208 by inserting distal end 278a through deployment knob lumen 272 and through lumen 254 of inserter grip 250 and inner sleeve 252 until threads 280 enter threaded opening 238a of anchor plate 208. Pull rod knob 282 is rotated in a clockwise motion to thread pull rod threads 280 into threaded anchor plate opening 238a. The measurement of depth stop 138, as observed and noted on indicator device 158 of disc preparation tool 100, is then transferred to inserter assembly 200. As such, where, for example, a marking 160 of indicator device 158 is observed through the "2" window, such reading is transferred to the "2" window of indicator device 336 of inserter assembly 200. This establishes the distance, D, as described hereinabove, that proximal surface 210a, 212a of cage implant 204 is spaced from shoulder 318 of inserter assembly 200. Having transferred the depth reading, cage implant 204 is manipulated by inserter grip 250 into the prepared disc space 342 until shoulder 318 contacts exterior anterior surface 338c of vertebra 338. This then establishes the spacing, $X_1$ between anchor penetration tips 240b, 242b and shoulder 318 of inserter assembly 200. At this point, anchor blade penetration tips 240b, 242b are precisely aligned with slots 344 formed at the scored locations in respective vertebral endplates 338a, 340a, as shown in FIG. 15.

Having suitably positioned cage implant to 204 in disc space 342 and aligned anchor blade penetration tips 240b, 242b with slots 344, anchor blades 240, 242 are then deployed. Such deployment is effected, as described above, by clockwise rotation of deployment knob 270. Such rotation of deployment knob 270 draws pull rod 278 in the proximal direction, deploying anchor blades 240 and 242 to the deployed second position, such that anchor blade penetration tips 240b, 242b penetrate into vertebral bodies 338b, 340b through scored locations 344, as shown in FIG. 16. After completion of the deployment of anchor blades 240, 242, elongate inserter 202 is separated from cage implant 204 by proximal movement of hook actuator 314, as explained above. With cage implant 204 suitably inserted in disc space 342, and anchor blades 240, 242 properly deployed, bone graft or other suitable fusion promotion materials may be introduced into opening 216 of cage implant 204 and around anchor plate 208. A cap 346, as shown in FIG. 17 may be attached to the proximal end of cage implant 204 so as to provide a barrier to maintain bone graft material in place within cage implant opening 216. Attachment of cap 346 to cage implant 204 may be effected by using cage implant windows 230, 234 and or channel 232, 236 as attachment surfaces.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A disc preparation instrument for use in fusing together a superior vertebra and an inferior vertebra, the superior vertebra including an inferior endplate and a vertebral body, the inferior vertebra including a superior endplate and a vertebral body, the superior and inferior endplates defining a disc space therebetween, the disc preparation instrument comprising:
an elongate handle having a distal end and a proximal end, and a trial device supported by said handle at the distal end thereof,
wherein said trial device comprises a trial body of size and configuration approximating the size and configuration of a cage implant for insertion into said disc space, said body having a distal surface, a proximal surface, a top surface and a bottom surface, said top surface having a top opening and said bottom surface having a bottom opening, said body including a movable scoring element having a first portion and a second portion, said scoring element being selectively movable from a first position wherein said first portion and said second portion are disposed interiorly of said device to a second position wherein said first portion extends exteriorly of said body through said top opening for scoring said inferior endplate of said superior vertebra at an upper scored location and said second portion extends exteriorly of said body through said bottom opening for scoring said superior endplate of said inferior vertebra at a lower scored location; and
wherein said handle comprises an elongate shaft extending within said handle, said shaft having a distal end extending into said body and attached to said scoring element, said shaft having an actuator at a proximal end, said actuator being operable to move said shaft and thereby said scoring element at the distal end thereof, said handle supporting a movable depth stop disposed adjacent to the distal end of said handle and being sized and configured to engage an exterior surface of one of said vertebrae when said trial device is disposed in said disc space, said handle having an adjustment knob operable to axially move said depth stop along said handle, said depth stop being spaced axially from said proximal surface of said trial body by a distance that is adjustable upon operation of said adjustment knob, said handle comprising an inner sleeve and an outer sleeve, said inner sleeve being attached to said trial body at a distal end thereof and having a lumen through which said shaft extends, said outer sleeve being movable axially along said inner sleeve and supporting said depth stop at a distal end thereof, said adjustment knob being supported on said outer sleeve for limited axial movement relative to said outer sleeve and said inner sleeve, said adjustment knob being biased axially against said inner sleeve to thereby form in a normal state a releasable lock preventing inadvertent axial movement of said outer sleeve relative to said inner sleeve.

2. The disc preparation instrument of claim 1, wherein said outer sleeve is coupled to said inner sleeve in a manner to allow limited relative axial translation but no relative rotation between said outer sleeve and said inner sleeve.

3. The disc preparation instrument of claim 1, wherein said scoring element is rotatable from said first position to said second position, said actuator comprising a rotatable T-handle at the proximal end of said handle for rotating said scoring element.

4. The disc preparation instrument of claim 3, wherein said T-handle is oriented with respect to said scoring element in a manner to visually determine when said scoring element is in said first position or said second position.

5. The disc preparation instrument of claim 1, wherein said adjustment knob is rotatably coupled to said outer sleeve to cause axial movement of said outer sleeve and thereby said depth stop relative to said inner sleeve upon rotation of said adjustment knob.

6. The disc preparation instrument of claim 5, wherein said releasable lock comprises a spring to provide an axial bias force that normally causes said adjustment knob to contact said inner sleeve, wherein said axial bias force may be manually overcome in a manner to move said adjustment knob away from contact with said inner sleeve in an opposite axial direction and thereby allow said outer sleeve to move axially relative to said inner sleeve.

7. The disc preparation instrument of claim 1, wherein said handle comprises an indicator device operable with the movement of said depth stop to provide a visual indication of a plurality of selectable distances between the proximal surface of said trial body and said depth stop, each distance being denoted by a different indicator.

8. The disc preparation instrument of claim 1, wherein said first portion and said second portion of said scoring element each comprise a rasped surface.

9. The disc preparation instrument of claim 6, wherein said releasable lock comprises an engagement surface on said adjustment knob and a locking surface on said inner sleeve.

10. The disc preparation instrument of claim 9, wherein each of said engagement surface and said locking surface comprises plural surfaces in a hex configuration.

11. A disc preparation instrument for use in fusing together a superior vertebra and an inferior vertebra, the superior vertebra including an inferior endplate and a vertebral body, the inferior vertebra including a superior endplate and a vertebral body, the superior and inferior endplates defining a disc space therebetween, the disc preparation instrument comprising:
an elongate handle having a distal end and a proximal end, and a trial device supported by said handle at the distal end thereof,
wherein said trial device comprises a trial body of size and configuration approximating the size and configuration of a cage implant for insertion into said disc space, said body having a distal surface, a proximal surface, a top surface and a bottom surface; and
wherein said handle supports a movable depth stop disposed adjacent to the distal end of said handle and being sized and configured to engage an exterior surface of one of said vertebrae when said trial device is disposed in said disc space, said handle having an adjustment member operable to axially move said depth stop along said handle, said depth stop being spaced axially from said proximal surface of said trial body by a distance that is adjustable upon operation of said adjustment knob, said handle comprising an inner sleeve and an outer sleeve, said inner sleeve being attached to said trial body at a distal end thereof, said outer sleeve being movable axially along said inner sleeve and supporting said depth stop at a distal end thereof, said handle comprising an indicator device operable with the movement of said depth stop to provide a visual indication of a plurality of selectable distances between the proximal surface of said trial body and said depth stop, said indicator device including a plurality of markings on said inner sleeve that are spaced axially at different distances from each other and a plurality of windows through said outer sleeve that are spaced from each other at approximately the same distance, whereby upon movement of said outer sleeve relative to said inner sleeve only one marking at a time will be aligned with a respective window such that each of said selectable distances is denoted by a different marking and window.

12. The disc preparation instrument of claim 11, wherein said outer sleeve is coupled to said inner sleeve in a manner to allow limited relative axial translation but no relative rotation between said outer sleeve and said inner sleeve.

13. The disc preparation instrument of claim 11, wherein said adjustment member comprises a knob rotatably coupled to said outer sleeve to cause axial movement of said outer sleeve and thereby said depth stop relative to said inner sleeve upon rotation of said adjustment knob.

14. The disc preparation instrument of claim 13, wherein said handle comprises a releasable lock between said adjustment knob and said inner sleeve to prevent inadvertent axial movement of said outer relative to said inner sleeve.

15. The disc preparation instrument of claim 14, wherein said releasable lock comprises a spring.

16. The disc preparation instrument of claim 11, further comprising a movable scoring element selectively movable from a first position to a second position for scoring said inferior endplate of said superior vertebra and for scoring said superior endplate of said inferior vertebra.

17. The disc preparation instrument of claim 16, wherein said scoring element comprises a rasped surface.

* * * * *